United States Patent
Gong et al.

(10) Patent No.: US 12,241,823 B2
(45) Date of Patent: Mar. 4, 2025

(54) METHODS FOR PREDICTING CRITICAL CAKING CYCLE OF CRYSTAL PARTICLE

(71) Applicants: TIANJIN UNIVERSITY, Tianjin (CN); ZHEJIANG HUAKANG PHARMACEUTICAL CO., LTD., Zhejiang (CN); ZHEJIANG INSTITUTE OF TIANJIN UNIVERSITY (SHAOXING), Zhejiang (CN)

(72) Inventors: Junbo Gong, Tianjin (CN); Mian Li, Quzhou (CN); Mingyang Chen, Shaoxing (CN); Wulong Yang, Quzhou (CN); Jiahui Li, Tianjin (CN); Mingxuan Li, Tianjin (CN); Qiang Wu, Quzhou (CN); Baohong Hou, Tianjin (CN); Qiuxiang Yin, Tianjin (CN)

(73) Assignees: TIANJIN UNIVERSITY, Tianjin (CN); ZHEJIANG HUAKANG PHARMACEUTICAL CO., LTD., Quzhou (CN); ZHEJIANG INSTITUTE OF TIANJIN UNIVERSITY (SHAOXING), Shaoxing (CN)

( * ) Notice: Subject to any disclaimer, the term of this patent is extended or adjusted under 35 U.S.C. 154(b) by 0 days.

(21) Appl. No.: 18/657,771

(22) Filed: May 7, 2024

(65) Prior Publication Data
US 2024/0344954 A1 Oct. 17, 2024

Related U.S. Application Data

(63) Continuation of application No. PCT/CN2023/106203, filed on Jul. 6, 2023.

(30) Foreign Application Priority Data

Oct. 20, 2022 (CN) .......................... 202211289850.9

(51) Int. Cl.
*G01N 15/06* (2024.01)
(52) U.S. Cl.
CPC .................................. *G01N 15/06* (2013.01)
(58) Field of Classification Search
CPC .............................. G01N 15/06; G01N 15/00
See application file for complete search history.

(56) References Cited

U.S. PATENT DOCUMENTS

| 7,187,441 B1 | 3/2007 | Sevick-Muraca et al. |
| 8,420,403 B2 * | 4/2013 | Hirano ..................... C01D 7/42 436/139 |

(Continued)

FOREIGN PATENT DOCUMENTS

| CN | 105466835 A | 4/2016 |
| CN | 105784480 A | 7/2016 |

(Continued)

OTHER PUBLICATIONS

Wang Wei, "Soy Sauce Powder Production By Spray Drying and Powder Property Characterization for Anti-Caking", 2012, Journal of Food Engineering, pp. 1-183. (Year: 2012).*

(Continued)

*Primary Examiner* — Mohamed Charioui
(74) *Attorney, Agent, or Firm* — METIS IP LLC

(57) ABSTRACT

The present disclosure provides a technology field of caking of crystal particles, and in particular relates to a method for predicting a critical caking cycle of crystal particle. The method includes: establishing a CHS crystal bridge growth model database of a crystal particle with a same type of crystal particle to be predicted firstly, selecting existed data in the corresponding CHS crystal bridge growth model (Continued)

database based on an equivalent particle radius, a stored ambient temperature, and an environmental high and low humidity cycle condition of the crystal particle to be predicted, respectively, and calculating the critical caking cycle according to experience calculation equations, wherein a result obtained by calculation is a predicted critical caking cycle of the crystal particle to be predicted. The present disclosure has characteristics of time-saving, convenience, good universality, and high prediction accuracy, which can quickly predict the critical caking cycle of multi-particle crystal particle products under different humidity storage conditions within a week, resulting in greatly reducing time costs and providing guidance for storage of industrial crystal particle products.

6 Claims, 7 Drawing Sheets

(56) References Cited

U.S. PATENT DOCUMENTS

| | | | |
|---|---|---|---|
| 2003/0211027 A1* | 11/2003 | Yokoyama | C01D 7/42 423/422 |
| 2007/0105226 A1 | 5/2007 | Hirano et al. | |
| 2007/0178037 A1* | 8/2007 | Hirano | C01D 7/42 423/422 |

FOREIGN PATENT DOCUMENTS

| | | |
|---|---|---|
| CN | 106202675 A | 12/2016 |
| CN | 106503397 A | 3/2017 |
| CN | 107063906 A | 8/2017 |
| CN | 107121363 A | 9/2017 |
| CN | 108959817 A | 12/2018 |
| CN | 111157408 A | 5/2020 |
| CN | 111661856 A | 9/2020 |
| CN | 114965186 A | 8/2022 |
| CN | 115684484 A | 2/2023 |
| JP | 2004157086 A | 6/2004 |
| JP | 2008197852 A | 8/2008 |
| JP | 2020166706 A | 10/2020 |

OTHER PUBLICATIONS

International Search Report in PCT/CN2023/106203 mailed on Sep. 27, 2023, 8 pages.
Written Opinion in PCT/CN2023/106203 mailed on Sep. 27, 2023, 8 pages.
Wang, Qing et al., Predictive Model for Hygroscopicity of Contents in Guizhi Fuling Capsules, China Journal of Chinese Materia Medica, 45(2): 242-249, 2020.
Zeng, Lingping et al., Study on the Hygroscopicity Mechanism and Measurement Method of the Granulated Seasonings, China Condiment, 34(4): 85-89, 2009.
Li, Yanhua et al., Research Progress on the Interactions Among Particles and Caking Behavior of Food Powder, Journal of the Chinese Cereals and Oils Association, 34(3): 126-132, 2019.
Wang, Fan et al., Research progress on mesoscale nucleation process in solution crystallization, CIESC Journal, 73(6): 2318-2333, 2022.
Li, Jiahui et al., Rapidly evaluating the caking tendency of sugar alcohols by developing a crystal bridge growth model: A case study of xylitol, Food Chemistry, 2022, 10 pages.

* cited by examiner

METHODS FOR PREDICTING CRITICAL CAKING CYCLE OF CRYSTAL PARTICLE

CROSS-REFERENCE TO RELATED APPLICATIONS

This application is a Continuation of International Application No. PCT/CN2023/106203, filed on Jul. 6, 2023, which claims priority to Chinese Patent Application No. 202211289850.9, filed on Oct. 20, 2022, the contents of which are incorporated herein by reference in their entirety.

TECHNICAL FIELD

The present disclosure relates to a technology field of caking of crystal particles, and in particular relates to a method for predicting a critical caking cycle of crystal particles.

BACKGROUND

The caking of crystal particles refers to a process in which the crystal particles with good fluidity and dispersibility originally, aggregate with each other to form an irregular caking. The caking phenomenon of the crystal particles is easy to occur in a post-processing (i.e., a transportation, storage, and drying of the crystal particles) for crystal particle products, resulting in degradation of performance of the crystal particle products. Therefore, operations of determining critical caking cycles of the crystal particle under different temperature and humidity storage conditions and realizing a prediction of the critical caking cycle are crucial for guiding growth, storage, and transportation of the crystal particle products.

However, the prediction of the critical caking cycle of the crystal particle is realized mainly based on a correspondence relationship between an accelerated caking experimental process under a high temperature and high humidity in the laboratory and a caking rate under an actual storage environment. A whole experimental period is relatively long (e.g., months or even a year) and an experimental quantity is large. Meanwhile, a single experiment can only determine a critical caking cycle under a specific humidity cycle condition, which can not achieve fast and accurate prediction for particle groups under different temperature and humidity conditions. In addition, the critical caking cycle of the crystal particle shows a high correlation with a size of the crystal particle, and the current general knowledge is that the larger the size of the crystal particle, the longer the critical caking cycle is, while a quantitative mathematical relationship has not been established to realize a theoretical guidance of the caking process yet.

Therefore, it is desired to provide a method for predicting the critical caking cycle of the crystal particle, to realize fast and accurate prediction of the critical caking cycle of the crystal particle product with little experimental quantity and low overall cost.

SUMMARY

One or more embodiments in the present disclosure provides a method for predicting a critical caking cycle of crystal particle, wherein the method is executed by a processor, the method comprises: establishing a CHS crystal bridge growth model database of a crystal particle with a same type of crystal particle to be predicted, wherein the CHS crystal bridge growth model database includes: an equivalent particle radius corresponding to different particle size standards of the same type of crystal particles, a moisture absorption capacity of crystal particles with different equivalent particle radii under multiple ambient temperatures and multiple ambient humidity conditions, respectively, and reference critical caking cycles of the crystal particles with different equivalent particle radii under the multiple ambient temperatures and multiple humidity cycle conditions, respectively; matching with the CHS crystal bridge growth model database based on an equivalent particle radius, an actual ambient temperature, and an actual humidity cycle condition of the crystal particle to be predicted, respectively, and calculating a critical caking cycle of the crystal particle to be predicted by selecting a corresponding preset algorithm according to a match result; wherein the preset algorithm includes a first preset algorithm and the second preset algorithm.

In some embodiments, in response to matching the CHS crystal bridge growth model database based on the actual ambient temperature and the actual humidity cycle condition of the crystal particle to be predicted, obtaining a target same type of crystal particles with a same environmental temperature and humidity cycle condition as the actual environmental temperature and humidity cycle condition, respectively, and determining the critical caking cycle of the crystal particle to be predicted through the first preset algorithm according to equation (a):

$$\frac{N_1}{N_1'} = \left(\frac{R_{1e}}{R_{1e}'}\right)^4 \qquad \text{equation (a)}$$

In the equation (a), $R_{1e}$ represents an equivalent particle radius of the target same type of crystal particles, $R_{1e}'$ represents the equivalent particle radius of the crystal particle to be predicted, $N_1$ represents a reference critical caking cycle of the target same type of crystal particles under the actual environmental temperature and humidity cycle condition of the crystal particle to be predicted, $N_1'$ represents the critical caking cycle of the crystal particle to be predicted, and $N_1$ and $N_1'$ are an integer not less than 1, respectively;

In some embodiments, in response to matching the CHS crystal bridge growth model database based on the actual ambient temperature and the equivalent particle radius of the crystal particle to be predicted, obtaining a target same type of crystal particles with a same environmental temperature and equivalent particle radius as the actual environmental temperature and equivalent particle radius, respectively, and determining the critical caking cycle of the crystal particle to be predicted through the second preset algorithm according to equation (b):

$$\frac{N_1}{N_1'} = \left(\frac{R_{1e}}{R_{1e}'}\right)^4 \qquad \text{equation (b)}$$

wherein $$V_I = V_{RH2} - V_{RH1}; \qquad \text{equation (c)}$$
$$V_I' = V_{RH3} - V_{RH1}; \qquad \text{equation (d)}$$

In the equations (b), (c), and (d), $V_{RH2}$ represents a moisture absorption capacity of the target same type of crystal particles under a high humidity condition in a corresponding humidity cycle condition; $V_{RH3}$ represents a moisture absorption capacity of the target same type of crystal particles under a high humidity condition in the actual humidity cycle condition, wherein a low humidity condition in the corresponding humidity cycle condition is the same as a low humidity condition in the high humidity condition in the actual humidity cycle condition; $V_{RH1}$ represents a moisture absorption capacity of the target same type of crystal particles under a low humidity condition in the corresponding humidity cycle condition; $V_1$ represents a difference between the moisture absorption capacity of the target same type of crystal particles under the high humidity condition and the low humidity condition in the corresponding humidity cycle condition; $V_1'$ represents a difference between the moisture absorption capacity of the target same type of crystal particles under the high humidity condition and the low humidity condition in the actual humidity cycle condition; $N_2$ represents a reference critical caking cycle of the target same type of crystal particles in the corresponding humidity cycle condition; $N_2''$ represents a reference critical caking cycle of the target same type of crystal particles in the actual humidity cycle condition, and $N_2$ and $N_2''$ are an integer not less than 1, respectively;

wherein the high humidity condition in the multiple humidity cycle conditions in the CHS crystal bridge growth model database is lower than a deliquescence point of the target same type of crystal particles such that the reference critical caking cycle is greater than once when a particle size of the target same type of crystal particles is less than 100 microns, the low humidity condition in the multiple humidity cycle conditions is less than the high humidity condition, and a humidity difference between the low humidity condition and the high humidity condition is greater than 20%.

In some embodiments, the equivalent particle radius of the target same type of crystal particles and the equivalent particle radius of the crystal particle to be predicted in the CHS crystal bridge growth model database are obtained by following operations: obtaining at least one particle size interval by performing particle size screening on crystal particles to be measured; determining a crystal quality and a count of crystal particles of the at least one particle size interval, and calculating an equivalent particle radius $R_e$ of the crystal particles to be measured according to equations (e) and (f):

$$P_1 R_1^3 + P_2 R_2^3 + \ldots + P_n R_n^3 = (P_1 + P_2 + \ldots + P_n) R_e^3; \quad \text{equation (e)}$$

$$P_1 R_1^3 : P_2 R_2^3 : \ldots : P_n R_n^3 = m_1 : m_2 : \ldots : m_n; \quad \text{equation (f)}$$

wherein $m_1, m_2, \ldots, m_n$ represent a crystal quality of (1-n)th particle size intervals, respectively, $P_1, P_2, \ldots, P_n$ represent a count of crystal particles of the (1-n)th particle size intervals, respectively, $R_1, R_2, \ldots, R_n$ represent a median radius value of the (1-n)th particle size intervals, respectively, n represents a count of particle size intervals, and Re represents the equivalent particle radius of the crystal particles.

In some embodiments, the reference critical caking cycle of the target same type of crystal particles with different equivalent particle radii under the multiple ambient temperatures and multiple humidity cycle conditions is obtained by: loading the target same type of crystal particles into a caking mold and placing the caking mold in a box with set temperature, setting a high humidity and low humidity in a high and low humidity cycle within the box being the same with the humidity cycle condition of the target same type of crystal particles, and setting a period of the high and low humidity cycle to 12-24 hours; counting a time of the high and low humidity cycle, and performing a de-molding operation for a caking of the target same type of crystal particles in the caking mold; during the de-molding operation, in response to the caking falls apart, determining that the caking of the target same type of crystal particles is not caked, and continuing to perform above cycle to a next cycle until the caking does not fall apart, and determining a count of cycles completed to prevent the caking from falling apart as a reference critical caking cycle of the target same type of crystal particles under a corresponding ambient temperature and humidity cycle condition.

In some embodiments, the determining the count of cycles completed to prevent the caking from falling apart as the reference critical caking cycle of the target same type of crystal particles under the corresponding ambient temperature and humidity cycle condition includes: in a same condition, determining the reference critical caking cycle repeatedly for three times, calculating an average of the reference critical caking cycles determined by three times, and designating the average as a reference critical caking cycle after averaging treatment.

In some embodiments, $V_{RH1}$, $V_{RH2}$, and $V_{RH3}$ in the equation (c) and equation (d) are calculated by: under a same ambient temperature, a same environmental humidity, and different equivalent particle radii, calculating a moisture absorption capacity $V_{RH}'$ of a target same type of crystal particle with an equivalent particle radius $R_e'$ under an environmental humidity condition RH based on following equation (g):

$$\frac{V_{RH}}{V_{RH}'} = \frac{R_e}{R_e'}, \quad \text{equation (g)}$$

wherein $V_{RH}$ represents a moisture absorption capacity of the target same type of crystal particles with the equivalent particle radius $R_e$ under the environmental humidity condition RH in the CHS crystal bridge growth model database, and $V_{RH}'$ is one of $V_{RH1}$, $V_{RH2}$, and $V_{RH3}$. In some embodiments, a determination of the moisture absorption capacity of the target same type of crystal particles is performed by a dynamic steam adsorption instrument, before the determination, performing an initial drying treatment for the target same type of crystal particles in advance, and a mass of the target same type of crystal particles does not exceed 10 mg.

In some embodiments, the crystal particle includes a xylitol crystal particle, and a high humidity condition of the humidity cycle condition for the xylitol crystal particle is 65% and a low humidity condition of the humidity cycle condition for the xylitol crystal particle is 30%.

One or more embodiments in the present disclosure provides a system for predicting a critical caking cycle of crystal particle, wherein the system includes a screening device, an environmental detection device, a processor, the system communicates with the environmental detection device and the processor, the processor is configured to generate and send screening instructions to control the screening device to perform particle size screening on crystal particle to be predicted; determine an equivalent particle radius of the crystal particle to be predicted based on the screened crystal particle to be predicted, generate detection instructions and send the detection instructions to the environmental detection device, wherein the environmental detection device is deployed in a storage space of the crystal particle to be predicted, the environmental detection device includes a temperature detection device and a humidity detection device, and the detection instructions are configured to control the temperature detection device and the humidity detection device to obtain a ambient temperature and humidity cycle conditions of the crystal particle to be predicted at a preset frequency, respectively; establishing a CHS crystal bridge growth model database of a crystal particle with a same type of crystal particle to be predicted, wherein the CHS crystal bridge growth model database includes: an equivalent particle radius corresponding to different particle size standards of the same type of crystal particles, a moisture absorption capacity of crystal particles with different equivalent particle radii under multiple ambient temperatures and multiple ambient humidity conditions, respectively, and reference critical caking cycles of the crystal particles with different equivalent particle radii under the multiple ambient temperatures and multiple humidity cycle conditions, respectively; matching with the CHS crystal bridge growth model database based on an equivalent particle radius, an actual ambient temperature, and an actual humidity cycle condition of the crystal particle to be predicted, respectively, and calculating a critical caking cycle of the crystal particle to be predicted by selecting a corresponding preset algorithm according to a match result; wherein the preset algorithm includes a first preset algorithm and the second preset algorithm.

In some embodiments, in response to matching the CHS crystal bridge growth model database based on the actual ambient temperature and the actual humidity cycle condition of the crystal particle to be predicted, obtaining a target same type of crystal particles with a same environmental temperature and humidity cycle condition as the actual environmental temperature and humidity cycle condition, respectively, and determining the critical caking cycle of the crystal particle to be predicted through the first preset algorithm according to equation (a):

$$\frac{N_1}{N_1'} = \left(\frac{R_{1e}}{R_{1e}'}\right)^4 \qquad \text{equation (a)}$$

In the equation (a), $R_{1e}$ represents an equivalent particle radius of the target same type of crystal particles, $R_{1e}'$ represents the equivalent particle radius of the crystal particle to be predicted, $N_1$ represents a reference critical caking cycle of the target same type of crystal particles under the actual environmental temperature and humidity cycle condition of the crystal particle to be predicted, $N_1'$ represents the critical caking cycle of the crystal particle to be predicted, and $N_1$ and $N_1'$ are an integer not less than 1, respectively;

In some embodiments, in response to matching the CHS crystal bridge growth model database based on the actual ambient temperature and the equivalent particle radius of the crystal particle to be predicted, obtaining a target same type of crystal particles with a same environmental temperature and equivalent particle radius as the actual environmental temperature and equivalent particle radius, respectively, and determining the critical caking cycle of the crystal particle to be predicted through the second preset algorithm according to equation (b):

$$\frac{N_1}{N_1'} = \left(\frac{R_{1e}}{R_{1e}'}\right)^4 \qquad \text{equation (b)}$$

wherein, $$V_1 = V_{RH2} - V_{RH1}; \qquad \text{equation (c)}$$

$$V_1' = V_{RH3} - V_{RH1}; \qquad \text{equation (d)}$$

In the equation (b), $V_{RH2}$ represents a moisture absorption capacity of the target same type of crystal particles under a high humidity condition in a corresponding humidity cycle condition; $V_{RH3}$ represents a moisture absorption capacity of the target same type of crystal particles under a high humidity condition in the actual humidity cycle condition, wherein a low humidity condition in the corresponding humidity cycle condition is the same as a low humidity condition in the high humidity condition in the actual humidity cycle condition; $V_{RH1}$ represents a moisture absorption capacity of the target same type of crystal particles under a low humidity condition in the corresponding humidity cycle condition; $V_1$ represents a difference of the target same type between the moisture absorption capacity of crystal particles under the high humidity condition and the low humidity condition in the corresponding humidity cycle condition; $V_1'$ represents a difference between the moisture absorption capacity of the target same type of crystal particles under the high humidity condition and the low humidity condition in the actual humidity cycle condition; $N_2$ represents a reference critical caking cycle of the target same type of crystal particles in the corresponding humidity cycle condition; $N_2''$ represents a reference critical caking cycle of the target same type of crystal particles in the actual humidity cycle condition, and $N_2$ and $N_2''$ are an integer not less than 1, respectively;

wherein the high humidity condition in the multiple humidity cycle conditions in the CHS crystal bridge growth model database is lower than a deliquescence point of the target same type of crystal particles such that the reference critical caking cycle is greater than once when a particle size of the target same type of crystal particles is less than 100 microns, the low humidity condition in the multiple humidity cycle conditions is less than the high humidity condition, and a humidity difference between the low humidity condition and the high humidity condition is greater than 20%.

One or more embodiments of the present disclosure provide a computer storage medium, the computer storage medium stores computer instructions, when the computer read the computer instructions in the storage medium, the computer performs a method for predicting a critical caking cycle of crystal particle.

BRIEF DESCRIPTION OF THE DRAWINGS

The present disclosure is further describable in terms of exemplary embodiments. These exemplary embodiments are describable in detail with reference to the drawings. These embodiments are non-limiting exemplary embodiments, in which like reference numerals represent similar structures throughout the several views of the drawings, and wherein

FIG. 4 is a schematic diagram illustrating a comparison between a measured result and a predicted result obtained by a CHS crystal bridge growth model database and a moisture absorption document of a xylitol crystal particle product according to some embodiments of the present disclosure;

DETAILED DESCRIPTION

In order to make the objects, technical solutions, and advantages of the present disclosure clearer and more understandable, the present disclosure is described in further detail hereinafter in conjunction with the accompanying drawings and embodiments. It should be understood that the specific embodiments described herein are only for explaining the present disclosure and are not intended to limit the present disclosure.

It will be understood that the term "system," "engine," "unit," "module," and/or "block" used herein are one method to distinguish different components, elements, parts, section or assembly of different level in ascending order. However, the terms may be displaced by another expression if they achieve the same purpose.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

Flowcharts are used in the present disclosure to illustrate the operation performed by the system according to the embodiment of the present disclosure. It should be understood that the preceding or subsequent operations are not necessarily performed accurately in sequence. Instead, the steps may be processed in reverse order or simultaneously. At the same time, other operations may add to these procedures, or remove one or more operations from these procedures.

Figure 1:
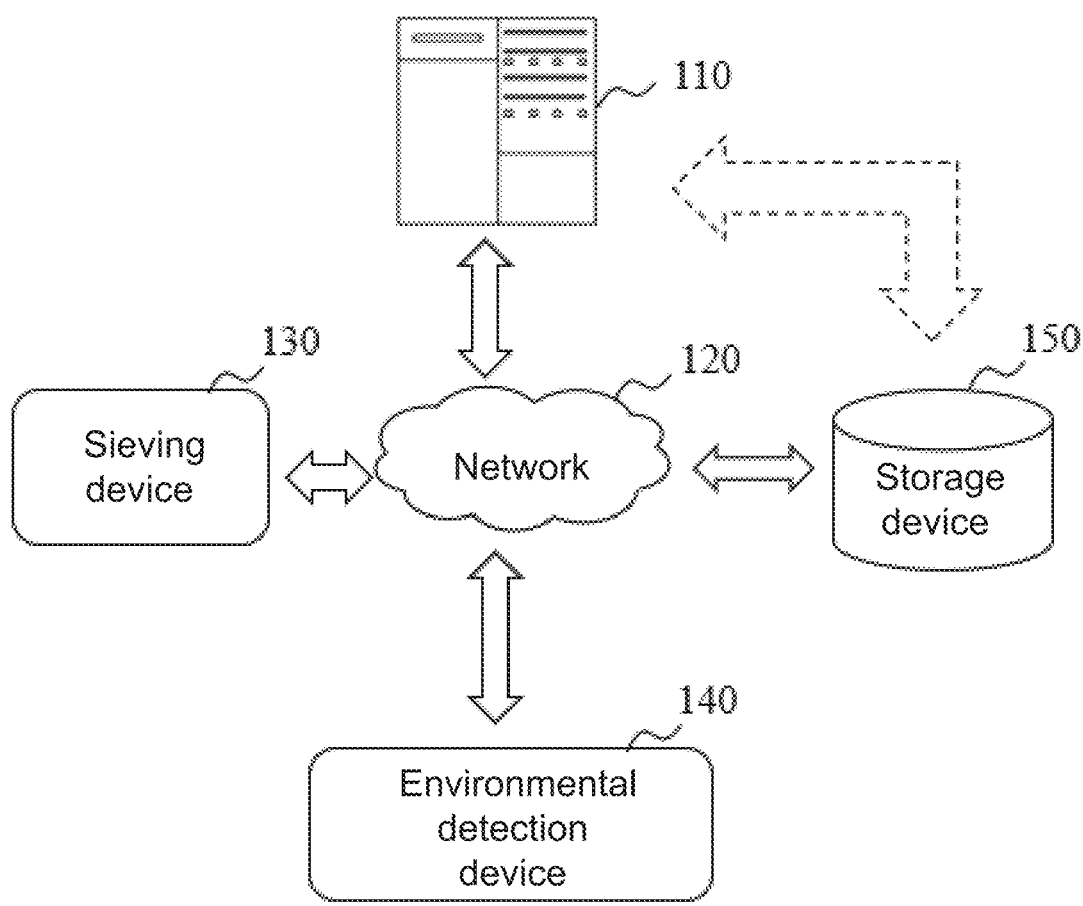
FIG. 1 is a schematic diagram illustrating an application scenario of a system for predicting a critical caking cycle of crystal particle according to some embodiments of the present disclosure.

FIG. 1 is a schematic diagram illustrating an application scenario of a system for predicting a critical caking cycle of crystal particle according to some embodiments of the present disclosure.

As shown in FIG. 1, an application scenario 100 may include a processor 110, a network 120, a sieving device 130, an environmental detection device 140, and a storage device 150. Components of the application scenario 100 may be connected in one or more of various ways. For example, the processor 110 may be connected to the storage device 150 via the network 120, as shown in FIG. 1. As another example, the processor 110 may be directly connected to the storage device 150, such that the processor 110 and the storage device 150 may be connected as indicated by dashed bi-directional arrows in FIG. 1.

In some embodiments, the processor 110 processes data and/or information obtained and/or extracted from the sieving device 130, the environmental detection device 140, the storage device 150, and/or other storage devices. For example, the processor 110 may obtain a particle size interval of crystal particles to be predicted from the sieving device 130. As another example, the processor 110 may obtain an actual ambient temperature and an actual humidity cycle condition of the crystal particle to be predicted from the environmental detection device 140. In some embodiments, the processor 110 may send instructions to control the sieving device 130 and the environmental detection device 140. For example, the processor 110 may send sieving instructions to control the sieving device 130 to set the crystal particles to be measured for performing particle size screening. For example, the processor 110 may send inspection instructions to control the environmental detection device 140 to obtain an actual ambient temperature and an ambient humidity of a storage space of the crystal particles to be predicted.

In some embodiments, the processor 110 may be a single server or a group of servers. The server group may be centralized or distributed. In some embodiments, the processor 110 may be local or remote. In some embodiments, the processor 110 may be implemented on a cloud platform. For example, a cloud platform may include a private cloud, a public cloud, a hybrid cloud, a community cloud, a distributed cloud, an on-premises cloud, a multi-tier cloud, or any combination thereof. In some embodiments, the processor 110 may be implemented on a computing device.

The network 120 may include any suitable network capable of facilitating the exchange of information and/or data of one or more components of the application scenario 100. In some embodiments, one or more components of the application scenario 100 (e.g., the processor 110, the sieving device 130, the environmental detection device 140, or the storage device 150) may communicate with one or more other components of the application scenario 100 to transmit information and/or data. In some embodiments, the network 120 may be any type of wired or wireless network or combination thereof.

The sieving device 130 is a device for performing the screening on crystal particles. In some embodiments, the sieving device 130 may perform the particle size screening on the crystal particles to be measured based on the sieving instructions. The crystal particles to be measured may include the crystal particle to be predicted and the same type of crystal particles. In some embodiments, the sieving device 130 may include a variety of aperture sizes. In some embodiments, the sieving device 130 may control sieving tools with different aperture disclosures to sieve the crystal particles in sequence according to the aperture size based on the sieving instructions issued by the processor. The sieving instruction may be a control instruction that controls the sieving device 130 to select sieves of different aperture disclosures to sieve the crystal particles in sequence according to the aperture size.

In some embodiments, the sieving device 130 may include multiple types of screening equipment, for example, the sieving device may include a stationary sieve, a vibrating sieve, a tumbler sieve, or the like.

The environmental detection device 140 is a device for detecting an environmental condition. The environmental detection device 140 may be configured to detect an ambient temperature, an ambient humidity, or the like. In some embodiments, the environmental detection device 140 may obtain the actual ambient temperature and the ambient humidity of the storage space of the crystal particles to be predicted based on the detection instructions. The detection instruction is a quality of control for controlling the environmental detection device 140 to obtain the actual environmental condition of the storage space. In some embodiments, the detection instruction may be configured to control the temperature detection device to obtain the actual ambient temperature of the storage space of the crystal particles to be predicted at a preset frequency. In some embodiments, the detecting instructions may also be configured to control the humidity detection device to obtain the ambient humidity of the storage space of the crystal particles to be predicted at a preset frequency. The preset frequency may be preset, for example, the preset frequency may be set to once every 5 minutes.

In some embodiments, the environmental detection device 140 may include a temperature detection device and a humidity detection device, the temperature detection device may include a temperature sensor, and the humidity detection device may include a humidity sensor. In some embodiments, the environmental detection device 140 may be deployed in a storage space of the crystal particle to be predicted.

The storage device 150 may store data and/or instructions. In some embodiments, the storage device 150 may store data obtained from the sieving device 130, the environmental detection device 140, and/or the processor 110. For example, the storage device 150 may store an actual ambient temperature, an ambient humidity, and a CHS crystal bridge growth model database of the storage space of the crystal particle to be predicted. In some embodiments, the storage device 150 may store data and/or instructions that the processor 110 may execute or use to perform the exemplary methods described in the present disclosure.

In some embodiments, the storage device 150 may include a mass storage device, a removable storage device, volatile read-write memory, read-only memory (ROM), or any combination thereof.

Figure 2:
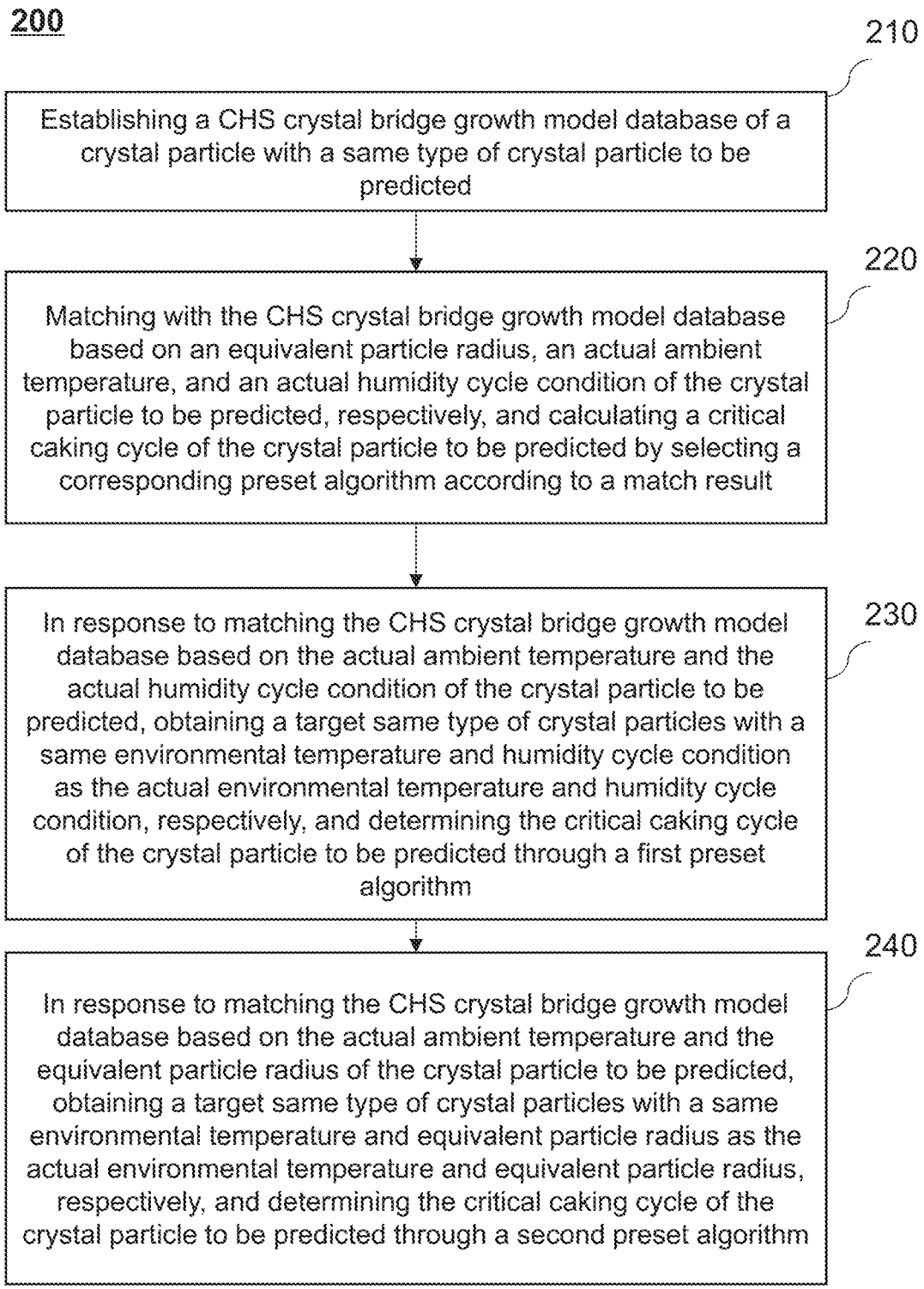
FIG. 2 is a schematic diagram illustrating an exemplary process for predicting a critical caking cycle of crystal particle according to some embodiments of the present disclosure.

FIG. 2 is a schematic diagram illustrating an exemplary process for predicting a critical caking cycle of crystal particle according to some embodiments of the present disclosure. In some embodiments, process 200 is executed by a processor. As shown in FIG. 4, the process 200 includes following operations In 210, CHS crystal bridge growth model database of crystal particle with a same type of crystal particle to be predicted may be established.

The crystal particle to be predicted is a crystal particle for which a critical caking cycle needs to be predicted.

In some embodiments, the crystal particle to be predicted may include a variety of types of the crystal particles, for example, the crystal particle to be predicted may include a xylitol crystal particle, a boron crystal, an aluminum silicate crystal, or the like.

The critical caking cycle is a time that a caking of crystal particles does not fall apart. In some embodiments, the critical caking cycle may be expressed by a count of cycles that have been completed or a length of time that the caking of crystal particles does not fall apart. The count of cycles is a count of unit cycles. A duration of the unit cycle may be preset, for example, a unit cycle may be 12 hours or 24 hours.

In some embodiments, the CHS crystal bridge growth model database of the same type of crystal particles of the crystal particles to be predicted may include an equivalent particle radius corresponding to different particle size standards of the same type of crystal particles, a moisture absorption capacity of crystal particles with different equivalent particle radii under multiple ambient temperatures and multiple ambient humidity conditions, respectively, and reference critical caking cycles of the crystal particles with different equivalent particle radii under the multiple ambient temperatures and multiple humidity cycle conditions, respectively.

In some embodiments, the processor may preset a plurality of the ambient temperatures, a plurality of the ambient humidity conditions, and randomly combine the plurality of the ambient temperatures, and plurality of the ambient humidity conditions to obtain a plurality of combinations of the different ambient temperatures and ambient humidity conditions, and stored in the CHS crystal bridge growth model database.

In some embodiments, the processor may preset the plurality of the ambient temperatures and the plurality of the humidity cycle conditions, and randomly combine the plurality of the ambient temperatures and the plurality of the humidity cycle conditions to obtain a plurality of combinations of the different ambient temperatures and humidity cycle conditions, and stored in the CHS crystal bridge growth model database. More description of the humidity cycle condition may be found in the following related description.

In some embodiments, the preset process may include one or more of random presetting, presetting based on historical data, presetting by a skilled professional, or the like.

The equivalent particle radius may be configured to characterize a radius of the crystal particle. It will be appreciated that when a shape of the crystal particle is an imperfect spherical shape the crystal particle has a certain physical property that is the same as or similar to that of the homogeneous spherical particles, the crystal particles of the imperfect spherical shape may be characterized by a radius of the spherical particles. The radius of the crystal particles may be characterized by the radius of the spherical particles. The radius of the spherical particles is the equivalent particle radius of the crystal particles.

In some embodiments, the equivalent particle radius of the same type of crystal particles in the CHS crystal bridge growth model database and the equivalent particle radius of the crystal particle to be predicted may be obtained by the following measurements, respectively: the processor may generate and send sieving instructions to the a sieving device to control the sieving device to perform particle size screening of the crystal particles to be measured to obtain at least one particle size interval; determining a mass and a count of the crystal particles of the at least one size interval; and the processor may calculate the equivalent particle radius Re of the crystal particles to be measured according to a predetermined radius determination algorithm. The crystal particles to be measured include the crystal particle to be predicted, and the crystal particles of the same type as the crystal particle to be predicted. The sieving instructions may be configured to control the sieving device to perform the particle size screening on the crystal particle to be measured.

A particle size interval is a certain range that characterizes a size of crystal particles. The mass of the particle size interval is a mass of the crystal particles within the particle size interval. In some embodiments, the mass of the particle size interval may be expressed as an average of the mass of crystal particles within the particle size interval. In some embodiments, the processor may measure the mass of crystal particles within the crystal mass size interval by a measurement device. The measurement device may include a balance. The count of the crystal particles in the particle size interval may be obtained statistically.

In some embodiments, the processor may determine the equivalent particle radius of the crystal particles to be measured based on the sieved crystal particles to be measured. The crystal particles to be measured include the crystal particles to be predicted and the same type of crystal particles. For example, the processor may determine the equivalent particle radius of the crystal particles to be predicted based on the sieved crystal particles to be predicted. As another example, the processor may determine the equivalent particle radius of the same type of crystal particles of the crystal particles to be predicted based on the sieved crystal particles to be predicted.

In some embodiments, the processor may calculate the equivalent particle radius Re of the crystal particles to be measured based on a preset radius determination algorithm, which may be associated with a mass and count of the crystal particles in the at least one particle size interval and a median radius value. For example, the preset radius determination algorithm may be represented by the following equations (e) and (f):

$$P_1 R_1^3 + P_2 R_2^3 + \ldots + P_n R_n^3 = (P_1 + P_2 + \ldots + P_n) R_e^3; \quad \text{equation (e)}$$

$$P_1 R_1^3 : P_2 R_2^3 : \ldots : P_n R_n^3 = m_1 : m_2 : \ldots : m_n; \quad \text{equation (f)}$$

wherein $m_1, m_2, \ldots, m_n$ represent a crystal quality of (1-n)th particle size intervals, respectively, $P_1, P_2, \ldots, P_n$ represent a count of crystal particles of the (1-n)th particle size intervals, respectively, $R_1, R_2, \ldots, R_n$ represent a median radius value of the (1-n)th particle size intervals, respectively, n represents a count of particle size intervals, and Re represents the equivalent particle radius of the crystal particles, Re represents an equivalent particle radius of crystal particles. The median radius value refers to a median radius value of crystal particles within the particle size interval.

In some embodiments of the present disclosure, the preset radius determination algorithm allows for more accurate and faster determination of the equivalent particle radius of the crystal particles.

The moisture adsorption capacity may be configured to characterize a moisture content of the crystal particles at a certain ambient temperature and ambient humidity condition.

In some embodiments, the moisture absorption capacity may be determined by a detection instrument. The processor may determine the moisture absorption capacity of the same type of crystal as the crystal to be predicted based on the detection instrument. The detection instrument may include a dynamic vapor adsorption apparatus, or the like.

In some embodiments, the processor may perform an initial drying treatment for the target same type of crystal particles before determining the moisture absorption capacity of the target same type of crystal particles by a dynamic steam adsorption instrument, and a mass of the target same type of crystal particles does not exceed 10 mg. The drying device may include a chamber dryer, a spray dryer, an airflow dryer, or the like.

In some embodiments, the processor may obtain the moisture absorption capacity of the same type of crystal particles with different equivalent particle radius in the CHS crystal bridge growth model database under multiple ambient temperatures and multiple ambient humidity conditions, respectively. For example, for each combination of the ambient temperatures and the ambient humidity conditions in the CHS crystal bridge growth model database, the processor may perform, based on the dynamic steam adsorption instrument, measure the moisture absorption capacity of the same type of crystal particles with different equivalent particle radii to obtain the moisture absorption capacity amount under the corresponding combination of the ambient temperature and the ambient humidity condition, and store the moisture absorption capacity in the CHS crystal bridge growth model database.

The humidity cycle condition refers to an ambient humidity interval for performing a high and low humidity cycle. The high and low humidity cycle condition refers to an ambient humidity alternates between high and low humidity. The humidity cycle condition may include a high humidity condition and a low humidity condition, and the high and low humidity cycle may occur within the interval between the high humidity condition and the low humidity condition. For example, the humidity cycle condition is 50%-30% if the high humidity condition is 50% and the low humidity condition is 30%.

In some embodiments, the processor may set the plurality of the humidity cycle conditions based on a preset rule and store is performed in the CHS crystal bridge growth model database. In some embodiments, the preset rule may include the low humidity condition in the humidity cycle condition being less than the high humidity condition, and a humidity difference between the low humidity condition and the high humidity condition being greater than 20%. In some embodiments, the preset rule may also include the high humidity condition being lower than a deliquescence point of the same type of crystal particles, such that the reference critical caking cycle of the same type of crystal particles with the particle size being less than 100 microns is greater than once. More description of the reference critical caking cycle may be found in the following related description.

In some embodiments, the preset rules corresponding to different types of the crystal particles may be different. In some embodiments, for the xylitol crystal particle, the corresponding preset rule may include a high humidity condition of 65% and the low humidity condition of 30% in the humidity cycle condition.

The reference critical caking cycle is the count of cycles that the caking does not fall apart under a certain ambient temperature and humidity cycle condition of the same type of crystal particles.

In some embodiments, the reference critical caking cycle of the same type of crystal particles of different equivalent particle radii in the CHS crystal bridge growth model database under multiple ambient temperatures and multiple humidity cycle conditions, respectively, may be obtained by following operations: the processor may select a combination of ambient temperature and humidity cycle condition, control an injection device to load the same type of crystal particles into the caking mold and place the caking mold in a box that has been set to have the same temperature as the ambient temperature, set the high and low humidity condition in the high and low humidity cycle in the box to be the same as the humidity cycle condition of the same type of crystal particles, and set the high and low humidity cycle; count the time of the high and low humidity cycle, and set the time of the high and low humidity cycle. At the end of each cycle of the high and low humidity cycle at the end of the cycle of each high and low humidity cycle, the caking of the same type of crystal particles in the caking mold is de-molded; in the process of de-molding operation, in response to the caking falls apart, determining that the caking of the target same type of crystal particles is not caked, and continuing to perform above cycle to a next cycle until the caking does not fall apart, and determining a count of cycles completed to prevent the caking from falling apart as a reference critical caking cycle of the target same type of crystal particles under a corresponding ambient temperature and humidity cycle condition. The period of the high and low humidity cycle may be from 12 hours to 24 hours to ensure that the moisture absorption of the crystal particles reaches equilibrium. The injection device is configured to load the same type of crystal particles into the caking mold and place the caking mold in a box with set temperature.

Figure 3:
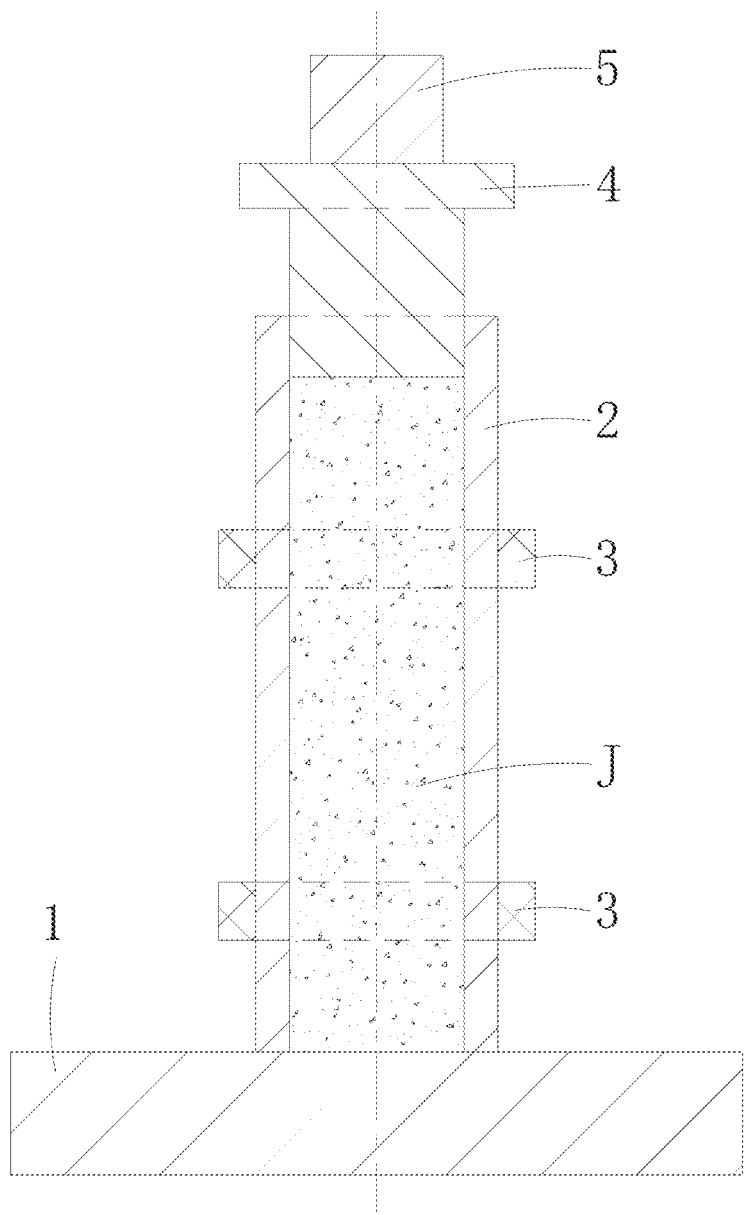
FIG. 3 is a schematic diagram illustrating a structure profile of a caking mold used for determining a critical caking cycle according to some embodiments of the present disclosure.

FIG. 3 is a schematic diagram illustrating a structure profile of a caking mold used for determining a critical caking cycle according to some embodiments of the present disclosure.

In some embodiments, as shown in FIG. 3, The caking mold may include a base 310, a cylindrical container 320 placed vertically on the base 310, a positioning sleeve 330 set around container 320 which is easy to disassemble, the container 320 may include a left housing and a right housing which is easy to demold, and the positioning sleeve 330 may fit the left housing and right housing together to form the container 320. A crystal particle product J to be measured is filled within the container 320, and multiple breathable small holes may be arranged on a side wall of the container 320 (not shown in the figure). An inner diameter of each breathable small hole may be smaller than a particle size of the crystal particle. A top of the crystal particle product may be provided with a pressing block 340, and a top of the pressing block 340 may be provided with a gravity weight 350. The pressing block 340 and the gravity weight 350 may simultaneously compress and compact the crystal particles in the container 320, making the crystal particles a caking. When performing demolding operations on the caking in the container 320, it is important to avoid applying additional stress to the caking, which can cause the caking to break and scatter, leading to misjudgment of the caking cycle.

The box may be configured to simulate a humidity change of the same type of crystal particles under the actual ambient temperature and humidity cycle conditions, allowing the same type of crystal particles to undergo dissolution recrystallization processes to form a crystal bridge. In some embodiments, the box is a constant temperature and humidity box.

In some embodiments, the processor may repeat the determination of the reference critical caking cycle at a preset count of times under the same conditions in accordance with the foregoing process, and calculate an average of the preset count of times of determination of the reference critical caking cycles, and use the average as the reference critical caking cycle after averaging treatment. The preset count of times may be preset, for example, the preset count of times may be 3. The processor may repeat the determination of the reference critical caking cycle three times under the same conditions, calculate an average of the three determined reference critical caking cycles, and use the average as the reference critical caking cycle after the averaging process.

In some embodiments of the present disclosure, determining the average of multiple determinations of the reference critical caking cycle as the reference critical caking cycle can reduce errors in the determinations caused by chance.

In some embodiments of the present disclosure, by simulating the humidity changes of the same type of crystal particles under actual ambient temperature and humidity cycle condition based on the caking mold and boxes, the more realistic reference critical caking cycle of the same type of crystal particles under multiple ambient temperatures and multiple humidity cycle conditions may be obtained respectively.

In 220, the CHS crystal bridge growth model database may be matched based on an equivalent particle radius, an actual ambient temperature, and an actual humidity cycle condition of the crystal particle to be predicted, respectively, and a corresponding preset algorithm may be selected according to a match result.

The actual ambient temperature refers to a temperature of the actual environment where the crystal particle to be predicted is located. The actual humidity cycle condition refers to a humidity cycle condition of the actual environment in which the crystal particle to be predicted is located. In some embodiments, the actual environment in which the crystal particle to be predicted is located may include a storage space for the crystal particle to be predicted.

In some embodiments, the processor may generate and send detection instructions to the environmental detection device to control the environmental detection device to perform data collection. In some embodiments, the environmental detection device may be deployed in a storage space of the crystal particle to be predicted.

In some embodiments, the detecting instructions may be configured to control the temperature detection device to obtain an actual ambient temperature of the storage space of the crystal particle to be predicted at a preset frequency. In some embodiments, the detecting instructions may also be configured to control the humidity detection device to obtain, at a preset frequency, an environmental humidity of the storage space of the crystal particle to be predicted. The preset frequency may be preset, e.g., the preset frequency may be set to once every 5 minutes.

In some embodiments, the processor may select a highest environmental humidity and a lowest environmental humidity of the plurality of the environmental humidities acquired by the humidity detection device, determine the highest ambient humidity as a high humidity condition in an actual humidity cycle condition, and determine the lowest ambient humidity as a low humidity condition in the actual humidity cycle condition.

In some embodiments, the processor may dynamically adjust a preset frequency based on an ambient temperature shift rate of the storage space. For example, the higher the ambient temperature shift rate, the faster the preset frequency. The ambient temperature shift rate may characterize a change rate of the ambient temperature.

In some embodiments, the processor may obtain a plurality of ambient temperatures collected at an initial preset frequency over a preset period of time, compute a change rate between any two ambient temperatures, obtain an average change rate by averaging the change average rates obtained by multiple calculations, and the average change rate may be determined as the change rate of the ambient temperature. The preset time may be set in advance, for example, the preset time may be set to the past 30 minutes.

In some embodiments, the processor may match the CHS crystal bridge growth model database based on an equivalent particle radius, an actual ambient temperature, and an actual humidity cycle condition of the crystal particle to be predicted, respectively. For example, the processor may match the CHS crystal bridge growth model database based on the actual ambient temperature and the actual humidity cycle condition of the crystal particle to be predicted, to obtain the same type of crystal particles with an ambient temperature and a humidity cycle condition being the same as the actual ambient temperature and the actual humidity cycle condition, respectively, wherein the equivalent particle radius of the crystal particle to be predicted is different from the equivalent particle radius of the target same type of crystal particles. As another example, the processor may match the actual ambient temperature and the equivalent particle radius of the crystal particle to be predicted with the CHS crystal bridge growth model database based on the actual ambient temperature and the equivalent particle radius of the crystal particle to be predicted to obtain the target same type of crystal particles with the ambient temperature and the equivalent particle radius being the same as the actual ambient temperature and the equivalent particle radius, respectively, wherein the actual humidity cycle condition of the crystal particle to be predicted may be different from the humidity cycle condition of target same type of crystal particles. More descriptions of the matching process may be found in FIG. 6 and the related descriptions.

The target same kind of crystal particle is homogeneous crystal particles in the database of CHS crystal bridge growth models that match the crystal particles to be predicted.

In some embodiments, the processor may calculate a critical caking cycle of the crystal particle to be predicted based on the match results. The preset algorithm may include a first preset algorithm and a second preset algorithm. More descriptions may be found in operation 230, operation 240, and the related descriptions. It should be noted that the operation 230 and the operation 240 are two different ways of calculating the critical caking cycle of the crystal particle to be predicted in the operation 220. The processor may execute either operation 230 or operation 240 after performing the operation 220 depending on the match condition.

In 230, in response to matching the CHS crystal bridge growth model database based on the actual ambient temperature and the actual humidity cycle condition of the crystal particle to be predicted, a target same type of crystal particles with a same environmental temperature and humidity cycle condition as the actual environmental temperature and humidity cycle condition, respectively may be obtained, and the critical caking cycle of the crystal particle to be predicted may be determined through the first preset algorithm.

In some embodiments, the first preset algorithm may be related to the equivalent particle radius of the target same type of crystal particles and the equivalent particle radius of the crystal particle to be predicted. For example, the first preset algorithm may be obtaining the critical caking cycle of the crystal particle to be predicted by calculating the equivalent particle radius of the target same type of crystal particles, the equivalent particle radius of the crystal particle to be predicted, and the reference critical caking cycle of the target same type crystal particles under the actual environmental condition of the crystal particle to be predicted. For example, the first preset algorithm may be represented by the following equation (a):

$$N_1' = N_1 \left( \frac{R_{1e}}{R_{1e}'} \right)^4 \quad \text{equation (a)}$$

In the equation (a), $R_{1e}$ represents an equivalent particle radius of the target same type of crystal particles, $R_{1e}'$ represents the equivalent particle radius of the crystal particle to be predicted, $N_1$ represents a reference critical caking cycle of the target same type of crystal particles under the actual environmental temperature and humidity cycle condition of the crystal particle to be predicted, $N_1'$ represents the critical caking cycle of the crystal particle to be predicted, and $N_1$ and $N_1'$ are an integer not less than 1, respectively.

In 240, in response to matching the CHS crystal bridge growth model database based on the actual ambient temperature and the equivalent particle radius of the crystal particle to be predicted, a target same type of crystal particles with a same environmental temperature and equivalent particle radius as the actual environmental temperature and equivalent particle radius, respectively may be obtained, and the critical caking cycle of the crystal particle to be predicted may be determined through the second preset algorithm.

In some embodiments, the second preset algorithm may be related with a difference between the moisture absorption capacity of the target same type of crystal particles under a high humidity condition and a low humidity condition in a corresponding humidity cycle condition, and a difference between the moisture absorption capacity of the crystal particle to be predicted under an actual high humidity condition and an actual low humidity condition in the actual humidity cycle condition. For example, the second preset algorithm may be a difference between the moisture absorption capacity of the target same type of crystal particles under the high humidity condition and the low humidity condition in the corresponding humidity cycle condition, a difference between the moisture absorption capacity of the crystal particle to be predicted under the high humidity condition and the low humidity condition in the actual humidity cycle condition, and the reference critical caking cycle of the target same type of crystal particles in the corresponding humidity cycle condition by calculating the critical caking cycle of the crystal particle to be predicted in the corresponding humidity cycle condition. For example, the second preset algorithm may be represented by the following equation (b):

$$\frac{N_2}{N_2''} = \frac{V_1'}{V_1}\bigg), \quad \text{equation (b)}$$

wherein, $$V_1 = V_{RH2} - V_{RH1}, \quad \text{equation (c);}$$

$$V_1' = V_{RH3} - V_{RH1}, \quad \text{equation (d);}$$

$V_{RH2}$ represents a moisture absorption capacity of the target same type of crystal particles under a high humidity condition in a corresponding humidity cycle condition; $V_{RH3}$ represents a moisture absorption capacity of the target same type of crystal particles under a high humidity condition in the actual humidity cycle condition, wherein a low humidity condition in the corresponding humidity cycle condition is the same as a low humidity condition in the high humidity condition in the actual humidity cycle condition; $V_{RH1}$ represents a moisture absorption capacity of the target same type of crystal particles under a low humidity condition in the corresponding humidity cycle condition; $V_1$ represents a difference between the moisture absorption capacity of the target same type of crystal particles under the high humidity condition and the low humidity condition in the corresponding humidity cycle condition; $V_1'$ represents a difference between the moisture absorption capacity of the target same type of crystal particles under the high humidity condition and the low humidity condition in the actual humidity cycle condition; $N_2$ represents a reference critical caking cycle of the target same type of crystal particles in the corresponding humidity cycle condition; $N_2''$ represents a reference critical caking cycle of the target same type of crystal particles in the actual humidity cycle condition, and $N_2$ and $N_2''$ are an integer not less than 1, respectively.

In some embodiments, $V_{RH1}$, $V_{RH2}$, and $V_{RH3}$ in the equations (c) and (d) may be calculated by the following process: the processor may calculate a moisture absorption capacity of same type of crystal particle with the equivalent particle radius of Re' under a fixed ambient humidity condition RH based on a preset moisture absorption algorithm $V_{RH}'$ under the same ambient temperature, same environmental humidity, and different equivalent particle radii.

In some embodiments, the preset moisture absorption algorithm may be related to the moisture absorption capacity of the same type of crystal particles in the CHS crystal bridge growth model database of the equivalent particle radius of $R_e$ at a fixed environmental humidity condition of RH. For example, the second preset algorithm may be one of $V_{RH1}$, $V_{RH2}$, and $V_{RH3}$ in the equations (c) and (d) obtained by calculating based on the moisture absorption capacity of the same type of crystal particles with the equivalent particle radius of $R_e$ in the CHS crystal bridge growth model database at a fixed environmental humidity condition of RH, the equivalent particle radius of R', and the equivalent particle radius of $R_e$. For example, the preset moisture absorption algorithm may be expressed by the following equation (g):

$$\frac{V_{RH}}{V_{RH}'} = \frac{R_e}{R_e'} \quad \text{equation (g)}$$

wherein $V_{RH}$ represents a moisture absorption capacity of the target same type of crystal particles with the equivalent particle radius $R_e$ under the environmental humidity condition RH in the CHS crystal bridge growth model database, and $V_{RH}'$ is one of $V_{RH1}$, $V_{RH2}$, and $V_{RH3}$.

In some embodiments of the present disclosure, the $V_{RH1}$, $V_{RH2}$, and $V_{RH3}$ in equations (c) and (d) above can be more accurately and quickly determined by the preset moisture absorption algorithm.

In some embodiments, the CHS crystal bridge growth model database may be used to predict the critical caking cycle of crystal particle to be predicted, which can realize fast and accurate prediction of the critical caking cycle of the crystal particle product, resulting in greatly reducing time costs and providing guidance for storage of industrial crystal particle products with good universality and high prediction accuracy.

It should be noted that the foregoing description of the process 200 is intended to be merely exemplary and illustrative, and does not limit the scope of application of the present disclosure. For those skilled in the art, various corrections and changes to the process hand-eye calibration may be made under the guidance of this disclosure. However, these corrections and changes remain within the scope of this disclosure.

In some embodiments, in response to the critical caking cycle satisfying a preset condition, the processor may generate and send adjustment instructions to the environmental adjustment device for adjusting the actual ambient temperature and the actual humidity cycle conditions of the crystal particle to be predicted. In some embodiments, the environmental adjustment device may be deployed in a storage space of the crystal particle to be predicted. In some embodiments, the environmental adjustment device may include, but is not limited to, at least one of a temperature detection device and a humidity detection device.

In some embodiments, the preset condition may include a critical caking cycle being less than a preset cycle threshold. The preset cycle threshold may be preset by technicians, for example, the preset cycle threshold may be 5 times.

The adjustment instructions may be control instructions used to control the environment adjustment device to adjust the environmental condition of the storage space. For example, one or more of the actual ambient temperatures and actual humidity cycle conditions for predicting the storage space of crystal particle may be adjusted. In some embodiments, the adjustment instruction may be used to control the environmental adjustment device to adjust the actual ambient temperature of the storage space according to the amount of temperature adjustment, and/or adjust the actual humidity cycle condition of the storage space according to a humidity cycle curve.

The amount of temperature adjustment refers to a numerical value of adjusting the actual ambient temperature. For example, the amount of temperature adjustment may be 10 C°.

The humidity cycle curve refers to a curve that characterizes the humidity cycle condition. A peak of the curve may be a high humidity condition under the humidity cycle condition, and a trough of the curve may be a low humidity condition under the humidity cycle condition.

In some embodiments, the processor may determine the amount of temperature adjustment and humidity cycle curve by querying a second correspondence table based on the difference between the critical caking cycle and the preset cycle threshold. In some embodiments, the second correspondence table may include a difference between the critical caking cycle and the preset cycle threshold and a correspondence between the amount of temperature adjustment and the humidity cycle curve. The second correspondence table may be preset by the processor based on historical data.

In some embodiments, the critical caking cycle of the crystal particle to be predicted may also be determined through various processes. For example, the processor may predict and determine the critical caking cycle of the crystal particle to be predicted through a prediction model. More descriptions of the prediction model may be found in FIG. 5 and related descriptions.

Figure 4A:
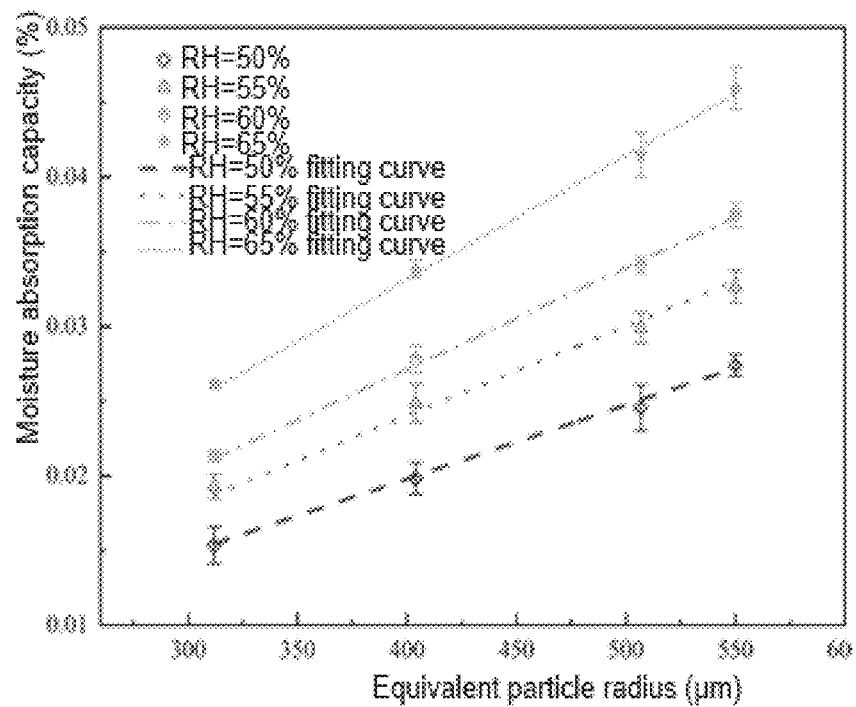
FIG. 4(a) is a schematic diagram illustrating a moisture curve of a xylitol crystal particle product at a temperature of 25° C. according to some embodiments of the present disclosure.

FIG. 4 is a schematic diagram illustrating a comparison between a measured result and a predicted result obtained by a CHS crystal bridge growth model database and a moisture absorption document of a xylitol crystal particle product according to some embodiments of the present disclosure; FIG. 4(a) is a schematic diagram illustrating a moisture curve of a xylitol crystal particle product at a temperature of 25° C. according to some embodiments of the present disclosure; FIG. 4(b) is a schematic diagram illustrating a comparison between a measured result and a predicted result of a moisture absorption capacity difference of a xylitol crystal particle and an equivalent particle radius according to some embodiments of the present disclosure; FIG. 4(c) is a schematic diagram illustrating a comparison between a measured result and a predicted result of a critical caking cycle and a moisture absorption capacity difference of a xylitol crystal particle according to some embodiments of the present disclosure; FIG. 4(d) is a schematic diagram illustrating a comparison between a measured result and a predicted result of a critical caking cycle and an equivalent particle radius of a xylitol crystal particle according to some embodiments of the present disclosure; FIG. 5 is a schematic diagram illustrating a fitting of predicted results of critical caking cycles of a multi-particle crystal product of a xylitol crystal particle according to some embodiments of the present disclosure. The following embodiments may be understood by referring to FIGS. 4 and 5, but the accompanying drawings are only a schematic representation of some of the embodiments and do not constitute a limitation on the embodiments.

An embodiment of the method for predicting a critical caking cycle of crystal particle provided in the present disclosure includes following operations:

A certain quality of xylitol crystal particle products may be taken, a metallic screen ranging from 500 microns to 600 microns may be selected based on the particle size and particle distribution characteristics of the xylitol crystal particle products for measuring a mass of each particle size interval and counting a count of crystal particles in each particle size interval, and the equivalent particle radius $R_e$ may be calculated to be 550 microns according to the equations (e) and (f). Moisture absorption characteristics of the crystal particle products may be measured by a dynamic steam adsorption instrument to obtain a moisture absorption characteristic file of the crystal particle products at a temperature of 25 C° as shown in FIG. 4(a). As shown in FIG. 4(a), a deliquescence point of the xylitol crystal particle may be around 75%. Therefore, the high humidity condition for a critical caking cycle experiment of the xylitol crystal particle may be set below 75%. The embodiments take an equivalent particle radius of 550 microns, temperature of 25 C°, and a stored environmental high and low humidity cycle condition of 65%~30% as an example to illustrate how to obtain and predict other equivalent particle radii, such as critical caking cycles of crystal particles of 312 microns, 404 microns, 507 microns, and 550 microns under different environmental high and low humidity cycle condition such as 65%~30%, 60%~30%, 55%~30%, and 50%~30%, and the critical caking cycles may be compared with measured results of the critical caking cycle to demonstrate the prediction accuracy of the process of the present disclosure.

A prediction process of the critical caking cycle in the embodiments includes:

In S1, a dynamic vapor adsorption instrument may be used to measure a moisture absorption capacity $V_{RH}$ of an equivalent particle radius of 550 microns under different humidity conditions. The crystal particles may be sieved through a metal sieve ranging from 500 microns to 600 microns. As shown in FIG. 4(a), at 30% humidity condition, the moisture absorption $V_{RH}$ is 0.02000%, at 50% humidity condition, the moisture absorption $V_{RH}$ is 0.02740%, at 55% humidity condition, the moisture absorption $V_{RH}$ is 0.03266%, at 60% humidity condition, the moisture absorption $V_{RH}$ is 0.03747%, and at 65% humidity condition, the moisture absorption $V_{RH}$ is 0.04595%. Subsequently, the crystal particle product may be loaded into a caking mold and the caking mold may be placed in the constant temperature and humidity box, an humidity condition of the constant temperature and humidity box may be set to 65%~30% alternating high and low humidity cycle, and a critical caking cycle N may be determined to be 7 times.

In S2, a calculation equation may be used to calculate and predict the critical caking cycle. The obtained parameters may be input into the CHS crystal bridge growth model database, according to an equation (g): $V_{RH}/V_{RH}'=R_e/R_e'$, moisture absorption capacities (i.e. a H-S file) of crystal particle products with different equivalent particle radii under the same humidity condition, calculation results may be shown in Table 1 below. For example, when a crystal particle with an equivalent particle radius of 312 microns is at 30% humidity, the moisture absorption capacity $V_{RH}$ is 0.01135%, when a crystal particle with an equivalent particle radius of 312 microns is at 50% humidity, the moisture absorption capacity $V_{RH}$ is 0.01554%, when a crystal particle with an equivalent particle radius of 312 microns is at 55% humidity, the moisture absorption capacity $V_{RH}$ is 0.01853%, when a crystal particle with an equivalent particle radius of 312 microns is at 60% humidity, the moisture absorption capacity $V_{RH}$ is 0.02126%, when a crystal particle with an equivalent particle radius of 312 microns is at 65% humidity, the moisture absorption capacity $V_{RH}$ IS 0.02607%. Calculation results of the moisture absorption capacities of other equivalent particle radii, such as crystal particles of 404 microns or 507 microns under different humidity environments may be shown in Table 1.

TABLE 1 moisture absorption capacities of crystal particles
with different equivalent particle radii

| $R_e$/(microns) | $V_{RH-30\%}$ | $V_{RH-50\%}$ | $V_{RH-55\%}$ | $V_{RH-60\%}$ | $V_{RH-65\%}$ |
|---|---|---|---|---|---|
| 550 | 0.02000 | 0.02740 | 0.03266 | 0.03747 | 0.04595 |
| 312 | 0.01135 | 0.01554 | 0.01853 | 0.02126 | 0.02607 |
| 404 | 0.01469 | 0.02013 | 0.02399 | 0.02752 | 0.03375 |
| 507 | 0.01844 | 0.02526 | 0.03011 | 0.03454 | 0.04236 |

It is now known that a critical caking cycle $N_1$ of crystal particles with an equivalent particle radius $R_{1e}$ of 550 microns under an environmental high and low humidity cycle condition of 65%~30% is 7 times, obtained parameters may be input into the CHS crystal bridge growth model database, according to the equation $$\frac{N_1}{N_1'} = \left(\frac{R_{1e}}{R_{1e}'}\right)^4, \quad (a)$$

a critical caking cycle $N_1'$ ((i.e., a C-S file) corresponding to crystal particles with an equivalent particle radius of $R_{1e}'$ under the same humidity RH condition may be calculated, and the critical caking cycle may be taken as an integer, for example, a critical caking cycle $N_1'$ of particle with an equivalent particle radius of 312 microns under a humidity cycle condition of 65%~30% is once, a critical caking cycle $N_1'$ of particle with an equivalent particle radius of 404 microns under the humidity cycle condition of 65%~30% is twice, and a critical caking cycle $N_1'$ of particle with an equivalent particle radius of 507 microns under the humidity cycle condition of 65%~30% is 5 times.

According to the H-S file and the equation (c): $V_1 = V_{RH2} - V_{RH1}$, a difference $V_1$ between the moisture absorption capacity of the crystal particles under single environmental high and low humidity cycle condition may be calculated, and a moisture absorption capacity difference $V_1$ of crystal particles with an equivalent particle radius of 550 microns may be calculated. Similarly, moisture absorption capacity differences $V_1$ of crystal particles with other equivalent particle radii under different environmental high and low humidity cycle conditions may be obtained, and calculation results are shown in Table 2.

TABLE 2 moisture absorption capacity differences $V_l$ of crystal
particles with different equivalent particle radii under
an environmental high and low humidity cycle condition

| $R_e$/(microns) | $V_l(50\%-30\%)$ | $V_l(55\%-30\%)$ | $V_l(60\%-30\%)$ | $V_l(65\%-30\%)$ |
|---|---|---|---|---|
| 550 | 0.00740 | 0.01266 | 0.01747 | 0.02595 |
| 312 | 0.00419 | 0.00718 | 0.00991 | 0.01472 |
| 404 | 0.00544 | 0.00930 | 0.01283 | 0.01906 |
| 507 | 0.00682 | 0.01167 | 0.01610 | 0.02392 |

The processor may integrate moisture absorption capacity difference $V_1$ and the C-S file of crystal particles with different equivalent particle radii under the environmental high and low humidity cycle condition, according to formula $$\frac{N_2}{N_2''} = \frac{V_l'}{V_l}, \quad (b)$$

a critical caking cycle $N_2''$ (i.e. a C—H file) may be calculated for the crystal particle products with the same equivalent particle radius under different environmental high and low humidity cycle conditions, and the critical caking cycle may be taken as an integer, and calculation results are shown in Table 3. For example, a moisture absorption capacity difference $V_1$ (65%-30%) of crystal particles with an equivalent particle radius of 550 microns is 0.02595, and the critical caking cycle $N_2$ under an environmental high and low humidity cycle condition of 65%-30% is 7 times, according to the Table 2, data of $V_1'(60\%-30\%)$ is 0.01747, according to the equation (b), a critical caking cycle $N_2''$ of crystal particles under an environmental high and low humidity cycle condition of 60%-30% is calculated to be 10 times. Similarly, critical caking cycles $N_2''$ under other conditions may be calculated.

TABLE 3 predicted results of critical caking cycles $N_2''$ of crystal
particles with different equivalent particle radii under different
environmental high and low humidity cycle conditions

| $R_e$/(microns) | $N_2''$ (50%-30%) | $N_2''$ (55%-30%) | $N_2''$ (60%-30%) | $N_2''$ (65%-30%) |
|---|---|---|---|---|
| 550 | 24 | 15 | 10 | 7 |
| 312 | 4 | 3 | 2 | 1 |
| 404 | 8 | 5 | 3 | 2 |
| 507 | 17 | 11 | 7 | 5 |

By integrating the data from the above files, a fitting diagram of predicted results of critical caking cycles of xylitol multi-particle crystal particle products under different environmental high and low humidity cyclic storage conditions may be shown as shown in FIG. 5.

In S3, the measured results of the critical caking cycle may be verified with the predicted values. A certain quality of xylitol crystal particle products may be taken, and based on the particle size and distribution characteristics of the crystal particle products, select metal sieves of 200 μm-300 μm, 300 μm-400 μm, and 400 μm-500 μm for screening, median radius values corresponding to the particle size intervals are 250 microns, 350 microns, and 450 microns, respectively. After sieving, the mass of crystal particles in each particle size interval may be weighed, and a mass ratio may be approximately 1:1:1, and the equivalent particle radius $R_e$ may be calculated from the mass ratio of crystal particles in each particle size interval, which is 312 microns. Then, the dynamic vapor adsorption instrument may be used to measure the moisture absorption capacity of the crystal particle products at humidity of 50%, 55%, 60%, and 65%, respectively. The critical caking cycle experiment may be conducted to set the environmental high and low humidity cycle conditions to 65%-30%, 60%-30%, 55%-30%, and 50%-30%, respectively, to determine the critical caking cycle. The measured critical caking cycle may be recorded.

Figure 4B:
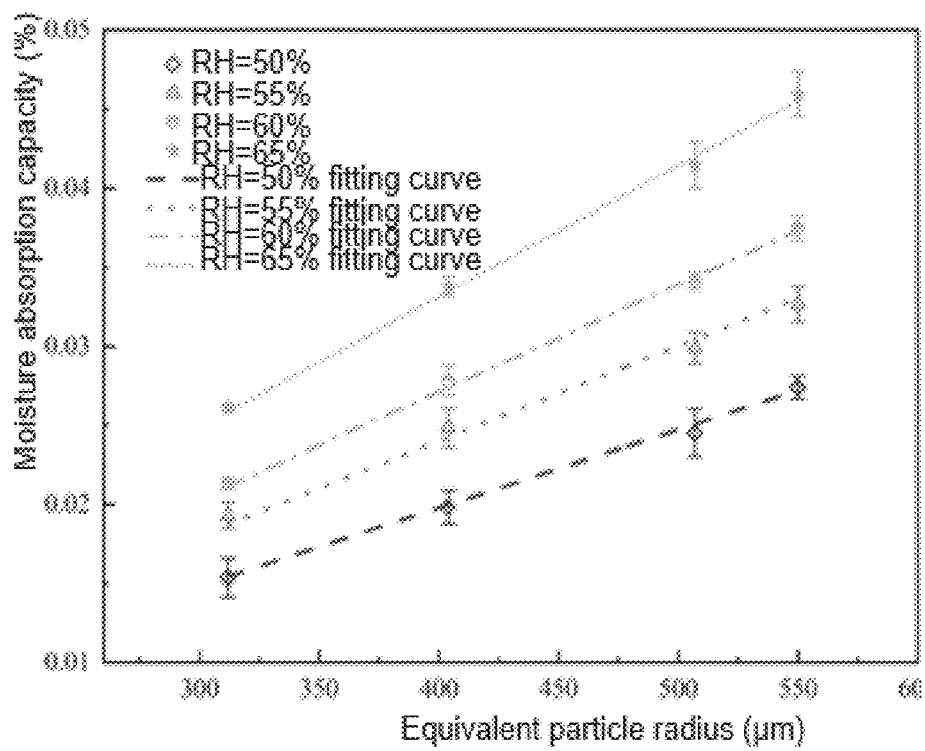
FIG. 4(b) is a schematic diagram illustrating a comparison between a measured result and a predicted result of a moisture absorption capacity difference of a xylitol crystal particle and an equivalent particle radius according to some embodiments of the present disclosure.
Figure 5:
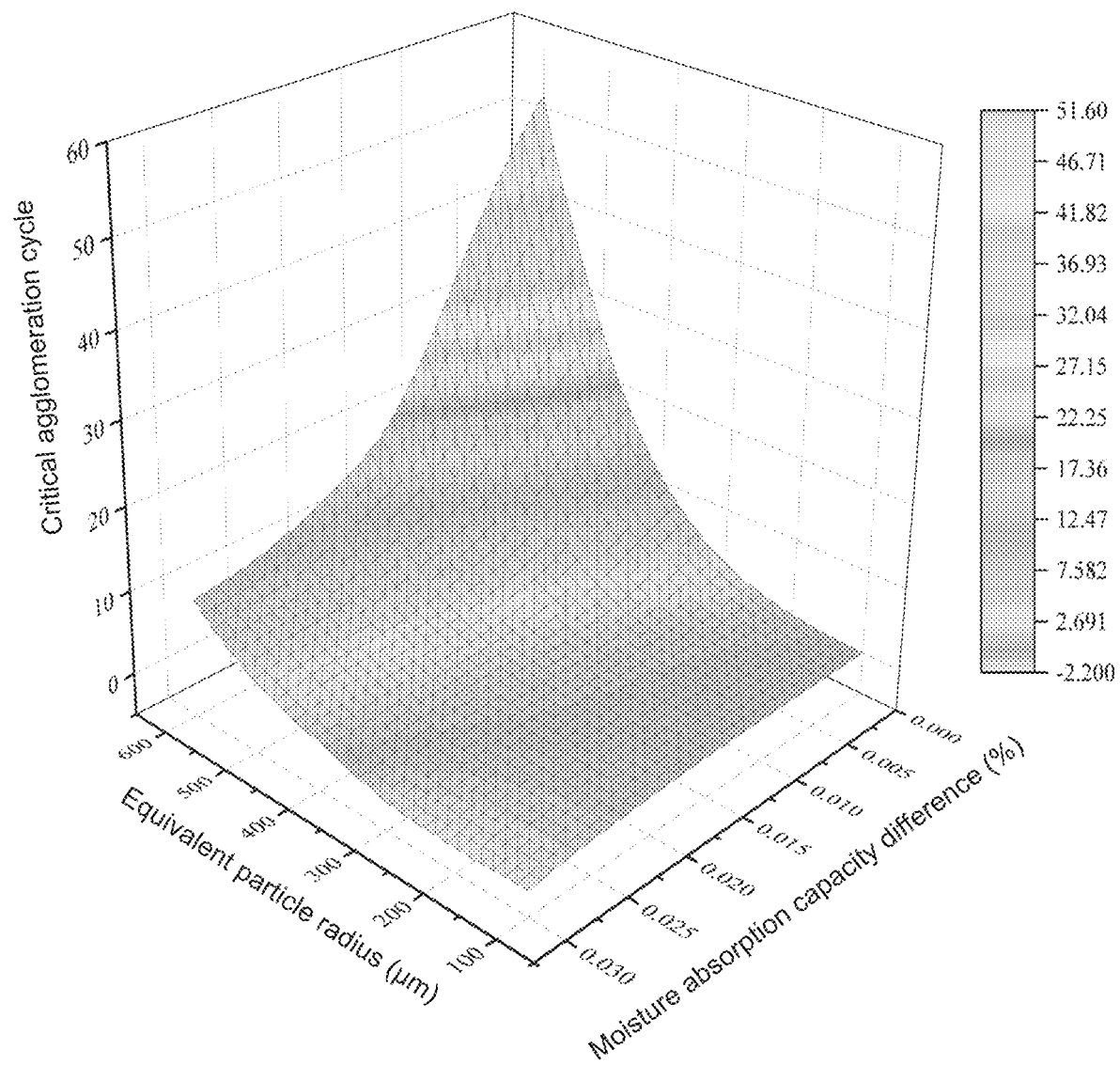
FIG. 5 is a schematic diagram illustrating a fitting of predicted results of critical caking cycles of a multi-particle crystal product of a xylitol crystal particle according to some embodiments of the present disclosure.

As shown in FIG. 4(b), the moisture absorption capacity of crystal particles may increase linearly with equivalent particle radii of 312 microns, 404 microns, 507 microns, and 550 microns at humidity of 50%, 55%, 60%, and 65%, respectively, which can fit well with the predicted result according to the equation $$\frac{V_{RH}}{V_{RH}'} = \frac{R_e}{R_e'}, \quad (g)$$

under humidity conditions of 50%, 55%, 60%, and 65%, fitted correlation coefficients may be 0.9966, 0.9896, 0.9982, and 0.9974, respectively, which is not less than 0.98, indicating a good fitting effect.

Figure 4C:
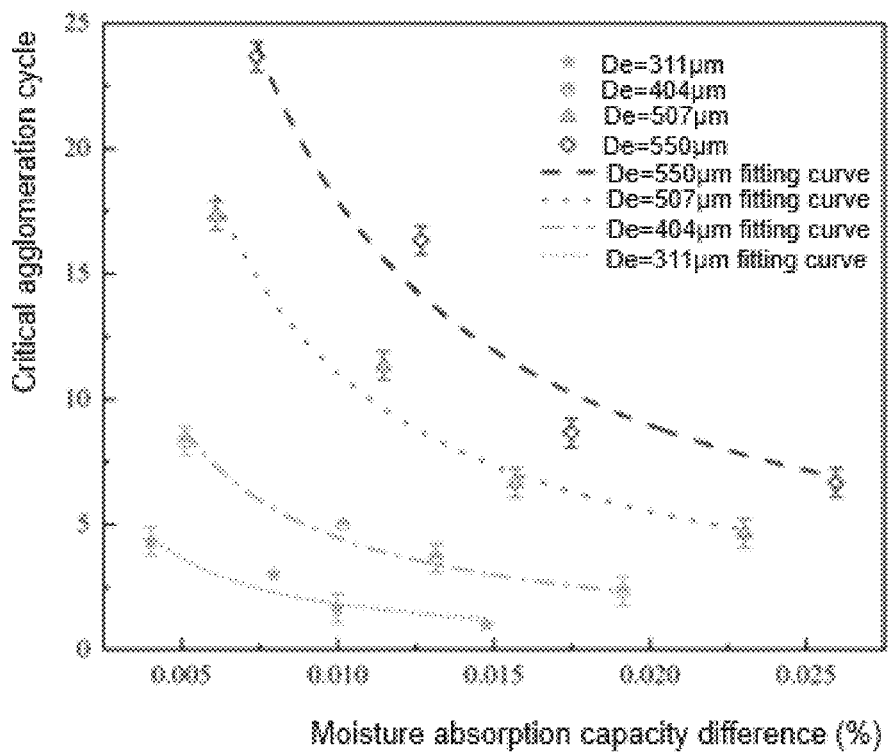
FIG. 4(c) is a schematic diagram illustrating a comparison between a measured result and a predicted result of a critical caking cycle and a moisture absorption capacity difference of a xylitol crystal particle according to some embodiments of the present disclosure.

As shown in FIG. 4(c), an inversely proportional relationship is between the moisture absorption capacity and the critical caking cycle, which can fit well with the predicted result according to the equation $$\frac{V_{RH}}{V'_{RH}} = \frac{R_e}{R'_e}, \quad (g)$$

fitted correlation coefficients of equivalent particle sizes of 311 μm, 404 μm, 507 μm, and 550 μm may be 0.9052, 0.9703, 0.9619, and 0.9578, which is not less than 0.90, indicating a good fitting effect.

Figure 4D:
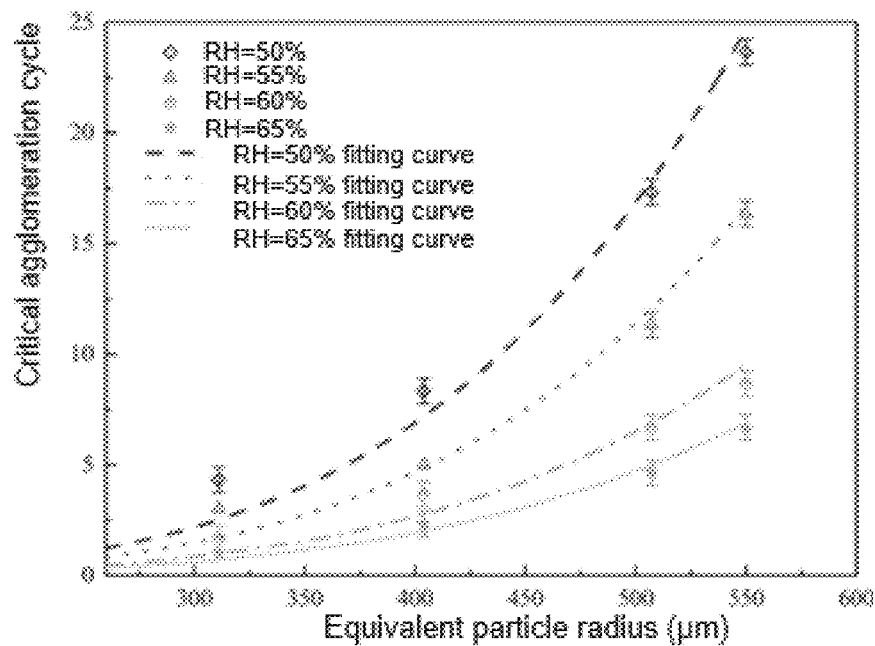
FIG. 4(d) is a schematic diagram illustrating a comparison between a measured result and a predicted result of a critical caking cycle and an equivalent particle radius of a xylitol crystal particle according to some embodiments of the present disclosure.

As shown in FIG. 4(d), a quadratic relationship is between the crystal particle size and the critical caking cycle, which can fit well with the predicted result according to the equation $$\frac{N_1}{N'_1} = \left(\frac{R_{1e}}{R'_{1e}}\right)^4. \quad (a)$$

Under high humidity cycle conditions of 50%, 55%, 60%, and 65%, the correlation coefficients may be 0.9767, 0.9679, 0.9035, and 0.9011, which is not less than 0.90, indicating a good fitting effect.

Therefore, the present disclosure uses the CHS crystal bridge growth model database to predict the critical caking cycle of multi-particle crystal product under different environmental high and low humidity cycle conditions has a relatively accurate prediction effect, small experimental quantity, and fast prediction speed.

Figure 6:
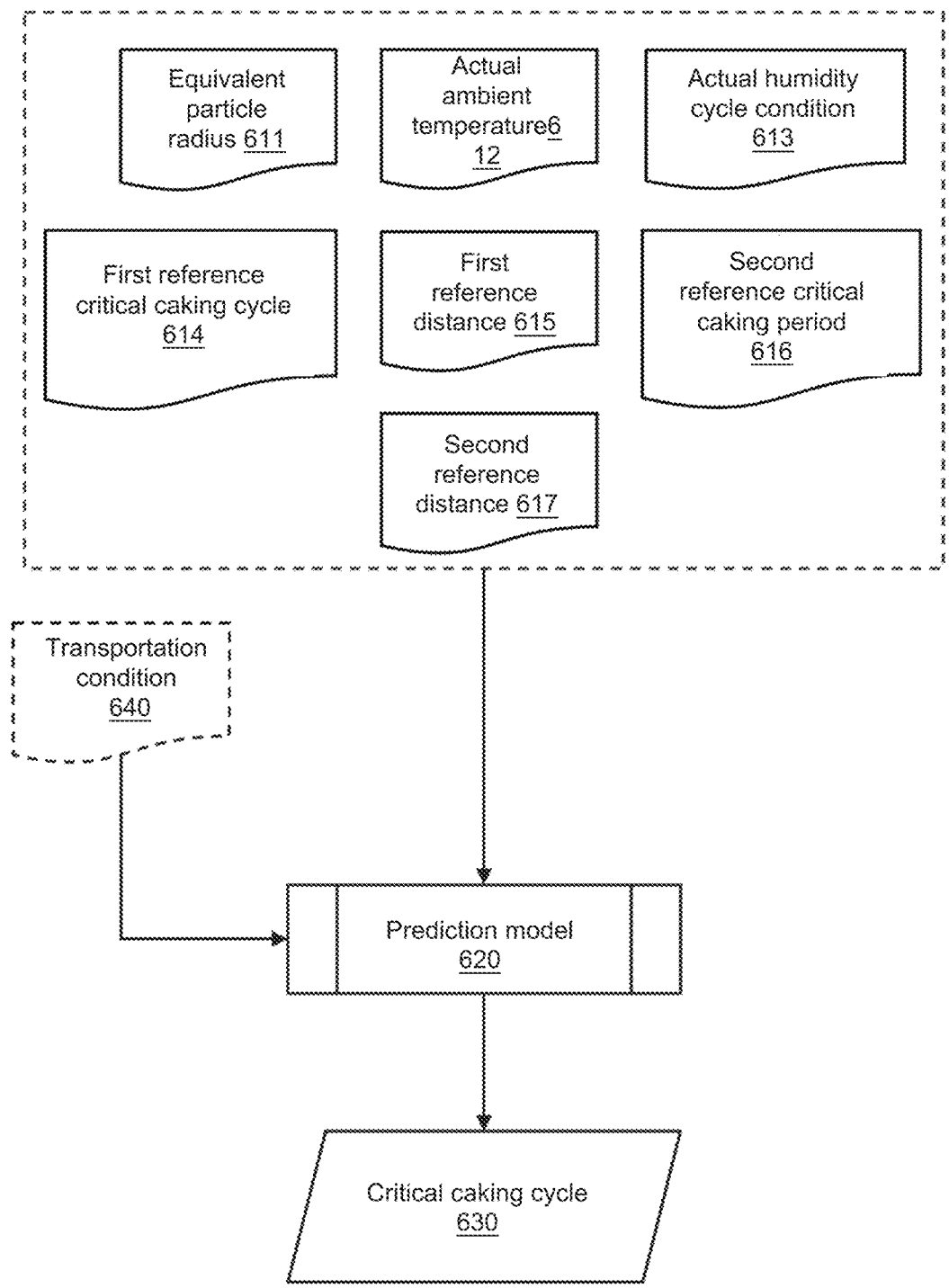
FIG. 6 is a schematic diagram illustrating an application prediction model according to some embodiments of the present disclosure.

FIG. 6 is a schematic diagram illustrating an application prediction model according to some embodiments of the present disclosure.

In some embodiments, as shown in FIG. 6, the processor may determine a critical caking cycle 630 of a crystal particle to be predicted based on an equivalent particle radius 611, an actual ambient temperature 612, an actual humidity cycle condition 613, a first reference critical caking cycle 614, a first reference distance 615, a second reference critical caking period 616, and a second reference distance 617 using a prediction model 620. The first reference critical caking cycle 614 is a reference critical caking cycle calculated based on a first sample reference. The first sample reference is a same type of crystal particles in the CHS crystal bridge growth model database that match the actual environmental temperature and humidity cycle conditions of the crystal particle to be predicted. The first reference distance 615 is a minimum vector distance between the first reference sample and the crystal particle to be predicted; the second reference critical caking cycle 616 is a reference critical caking cycle calculated based on a second sample reference. The second sample reference is a same type of crystal particles in the CHS crystal bridge growth model database that match the actual environmental temperature and equivalent particle radius of the crystal particle to be predicted. The second reference distance 617 is a minimum vector distance between the second sample reference and the crystal particle to be predicted.

In some embodiments, the processor may calculate the critical caking cycle of the crystal particle to be predicted based on the equivalent particle radius of the first sample reference, the reference critical caking cycle corresponding to the actual environmental temperature and humidity cycle condition of the crystal particle to be predicted in the first reference sample, and the equivalent particle radius of the crystal particle to be predicted by using the equation (a), the critical caking cycle may be determined as a first reference critical caking cycle.

In some embodiments, the processor may construct a feature vector based on the actual ambient temperature and actual humidity cycle condition of the crystal particle to be predicted, match reference vectors in the CHS crystal bridge growth model database and select a reference vector with a smallest vector distance from the feature vector, determine a same type of crystal particles corresponding to the reference vectors as the first sample reference, and determine a minimum vector distance as the first reference distance. The feature vector may include a numerical value of the actual environmental temperature, numerical values of the high humidity condition and low humidity condition in actual humidity cycle condition. The reference vectors may include a numerical value of ambient temperature corresponding to the same type of crystal particles and numerical values of the high humidity condition and low humidity condition in the humidity cycle condition.

In some embodiments, the processor may obtain a critical caking cycle $N_2$ based on a difference between the moisture absorption capacity of the second sample reference under a high humidity condition and a low humidity condition in the corresponding humidity cycle condition, respectively, a reference critical caking cycle under the corresponding humidity condition, a difference between a moisture absorption capacity of the crystal particle to be predicted under the high humidity condition and low humidity condition in the actual humidity cycle conditions, respectively, according to the equation (b), and the critical caking cycle $N_2$ may be determined as a second reference critical caking cycle.

In some embodiments, the processor may construct a feature vector based on the actual ambient temperature and the equivalent particle radius of the crystal particle to be predicted, match reference vectors in the CHS crystal bridge growth model database and select a reference vector with a smallest vector distance from the feature vector, determine a same type of crystal particles corresponding to the reference vectors as the second sample reference, and determine a minimum vector distance as the second reference distance. The feature vector may include a numerical value of the actual environmental temperature, a numerical value of the equivalent particle radius. The reference vectors may include numerical values of ambient temperature and equivalent particle radius corresponding to the same type of crystal particles.

The prediction model refers to a model used to determine the critical caking cycle of the crystal particle to be predicted. In some embodiments, the prediction model may be a machine learning model. For example, the prediction model may include any one or combination of neural networks (NN) model or other custom model structures.

In some embodiments, as shown in FIG. 6, an input of the prediction model 620 may include an equivalent particle radius 611, an actual ambient temperature 612, an actual humidity cycle condition 613, a first reference critical caking cycle 614, a first reference distance 615, a second reference critical caking cycle 616, and a second reference distance 617 of the crystal particle to be predicted, and an output may include a critical caking cycle 630 of the crystal particle to be predicted.

In some embodiments, as shown in FIG. 6, the input of the prediction model may also include a transportation condition 640. The transportation condition 640 refers to a condition related to the transportation of the crystal particle to be predicted. In some embodiments, the transportation condition 640 may include a type of transportation vehicle and a smoothness degree of transportation.

The smoothness degree of transportation refers to a stability of the transportation vehicle during a transportation process of the crystal particle to be predicted. In some embodiments, the processor may determine the smoothness degree of transportation by querying a first corresponding relationship table based on a speed change of the transportation vehicle. In some embodiments, the processor may calculate a speed standard deviation based on speeds of the transport vehicle at multiple times during the transportation, and the peed standard deviation represents a speed change of the transport vehicle. The processor may communicate with a control terminal of the transportation vehicle to obtain speed information of the transportation vehicle. The processor may also obtain the speed information of the transport vehicle by communicating with a speed sensor set on the transport vehicle.

In some embodiments, the first correspondence table may include a correlation between the speed standard deviation and the smoothness degree of transportation. For example, the correlation may be that the lower the speed standard deviation, the higher the smoothness degree of transportation. The first correspondence table may be preset by the processor based on historical data.

In some embodiments of the present disclosure, the transportation condition may be added to the input of the prediction model to consider possible changes in the critical caking cycle caused by transportation bumps when determining the critical caking cycle, thereby improving the accuracy of the prediction model.

In some embodiments, the model may be obtained by: obtaining multiple training samples with labels, and obtaining a trained prediction model by inputting the multiple training samples with labels into an initial prediction model for training. The training samples may include a sample equivalent particle radius of the sample crystal particles to be predicted, sample actual environmental temperature, a sample humidity cycle condition, a sample first reference critical caking cycle, a sample first reference distance, a sample second reference critical caking cycle, and a sample second reference distance; a different count of training samples correspond to different equivalent particle radius among the training samples; the labels may be actual critical caking cycles corresponding to the training samples.

In some embodiments, training samples may be obtained based on historical data, and the labels may be determined based on the historical actual critical caking cycle corresponding to the training samples.

In some embodiments, the training sample set may include training samples constructed based on crystal particles with different equivalent particle radii. The different count of training samples may correspond to different equivalent particle radii in the training sample set. For example, the larger the equivalent particle radius, the more corresponding training samples there are. It may be understood that, as shown in FIG. 2(d), under a fixed environmental humidity of RH, as the equivalent particle radius gradually increases, the change rate of the critical caking cycle increases, and the prediction accuracy may decrease. Therefore, more training samples are needed to train the prediction model.

In some embodiments of the present disclosure, the larger the equivalent particle radius, the more corresponding training samples there are, making the training samples more realistic and effective, which can improve the accuracy of the prediction model.

In some embodiments of the present disclosure, the critical caking cycle may be determined through the prediction model, which can provide more options for determining the critical caking cycle and improve the accuracy of predicting the critical caking cycle.

In some embodiments of the present disclosure further provides a system for predicting a critical caking cycle of crystal particle, wherein the system includes a screening device, an environmental detection device, a processor, the system communicates with the environmental detection device and the processor, the processor is configured to generate and send screening instructions to control the screening device to perform particle size screening on crystal particle to be predicted; determine an equivalent particle radius of the crystal particle to be predicted based on the screened crystal particle to be predicted, generate detection instructions and send the detection instructions to the environmental detection device, wherein the environmental detection device is deployed in a storage space of the crystal particle to be predicted, the environmental detection device includes a temperature detection device and a humidity detection device, and the detection instructions are configured to control the temperature detection device and the humidity detection device to obtain a ambient temperature and humidity cycle conditions of the crystal particle to be predicted at a preset frequency, respectively; establishing a CHS crystal bridge growth model database of a crystal particle with a same type of crystal particle to be predicted, wherein the CHS crystal bridge growth model database includes: an equivalent particle radius corresponding to different particle size standards of the same type of crystal particles, a moisture absorption capacity of crystal particles with different equivalent particle radii under multiple ambient temperatures and multiple ambient humidity conditions, respectively, and reference critical caking cycles of the crystal particles with different equivalent particle radii under the multiple ambient temperatures and multiple humidity cycle conditions, respectively; matching with the CHS crystal bridge growth model database based on an equivalent particle radius, an actual ambient temperature, and an actual humidity cycle condition of the crystal particle to be predicted, respectively, and calculating a critical caking cycle of the crystal particle to be predicted by selecting a corresponding preset algorithm according to a match result; wherein the preset algorithm includes a first preset algorithm and the second preset algorithm.

In some embodiments, the processor may be further configured to: in response to matching the CHS crystal bridge growth model database based on the actual ambient temperature and the actual humidity cycle condition of the crystal particle to be predicted, obtaining a target same type of crystal particles with a same environmental temperature and humidity cycle condition as the actual environmental temperature and humidity cycle condition, respectively, and determining the critical caking cycle of the crystal particle to be predicted through the first preset algorithm according to equation (a):

$$\frac{N_1}{N_1'} = \left(\frac{R_{1e}}{R_{1e}'}\right)^4, \quad \text{equation (a)}$$

in the equation (a), $R_{1e}$ represents an equivalent particle radius of the target same type of crystal particles, $R_{1e}$ represents the equivalent particle radius of the crystal particle to be predicted, $N_1$ represents a reference critical caking cycle of the target same type of crystal particles under the actual environmental temperature and humidity cycle condition of the crystal particle to be predicted, $N_1'$ represents the critical caking cycle of the crystal particle to be predicted, and $N_1$ and $N_1'$ are an integer not less than 1, respectively;

In some embodiments, the processor may be further configured to: in response to matching the CHS crystal bridge growth model database based on the actual ambient temperature and the equivalent particle radius of the crystal particle to be predicted, obtaining a target same type of crystal particles with a same environmental temperature and equivalent particle radius as the actual environmental temperature and equivalent particle radius, respectively, and determining the critical caking cycle of the crystal particle to be predicted through the second preset algorithm according to equation (b):

$$\frac{N_2}{N_2''} = \frac{V_I'}{V_I}, \quad \text{equation (b)}$$

wherein $$V_I = V_{RH2} - V_{RH1}, \quad \text{equation (c);}$$

$$V_I' = V_{RH3} - V_{RH1}, \quad \text{equation (d);}$$

In the equations (b), (c), and (d), $V_{RH2}$ represents a moisture absorption capacity of the target same type of crystal particles under a high humidity condition in a corresponding humidity cycle condition; $V_{RH3}$ represents a moisture absorption capacity of the target same type of crystal particles under a high humidity condition in the actual humidity cycle condition, wherein a low humidity condition in the corresponding humidity cycle condition is the same as a low humidity condition in the high humidity condition in the actual humidity cycle condition; $V_{RH1}$ represents a moisture absorption capacity of the target same type of crystal particles under a low humidity condition in the corresponding humidity cycle condition; $V_I$ represents a difference between the moisture absorption capacity of the target same type of crystal particles under the high humidity condition and the low humidity condition in the corresponding humidity cycle condition; $V_I'$ represents a difference between the moisture absorption capacity of the target same type of crystal particles under the high humidity condition and the low humidity condition in the actual humidity cycle condition; $N_2$ represents a reference critical caking cycle of the target same type of crystal particles in the corresponding humidity cycle condition; $N_2''$ represents a reference critical caking cycle of the target same type of crystal particles in the actual humidity cycle condition, and $N_2$ and $N_2''$ are an integer not less than 1, respectively;

wherein the high humidity condition in the multiple humidity cycle conditions in the CHS crystal bridge growth model database is lower than a deliquescence point of the target same type of crystal particles such that the reference critical caking cycle is greater than once when a particle size of the target same type of crystal particles is less than 100 microns, the low humidity condition in the multiple humidity cycle conditions is less than the high humidity condition, and a humidity difference between the low humidity condition and the high humidity condition is greater than 20%.

In some embodiments of the present disclosure provides a computer storage medium, the computer storage medium stores computer instructions, when the computer read the computer instructions in the storage medium, the computer performs a method for predicting a critical caking cycle of crystal particle.

In addition, certain features, structures, or features in one or more embodiments of this specification may be appropriately combined.

In some embodiments, numbers describing the number of ingredients and attributes are used. It should be understood that such numbers used for the description of the embodiments use the modifier "about", "approximately", or "substantially" in some examples. Unless otherwise stated, "about", "approximately", or "substantially" indicates that the number is allowed to vary by ±20%. Correspondingly, in some embodiments, the numerical parameters used in the description and claims are approximate values, and the approximate values may be changed according to the required characteristics of individual embodiments. In some embodiments, the numerical parameters should consider the prescribed effective digits and adopt the method of general digit retention. Although the numerical ranges and parameters used to confirm the breadth of the range in some embodiments of the present disclosure are approximate values, in specific embodiments, settings of such numerical values are as accurate as possible within a feasible range.

If there is any inconsistency or conflict between the description, definition, and/or use of terms in the materials cited in the present disclosure and the content described in the present disclosure, the description, definition, and/or use of terms in this manual shall prevail.

What is claimed is:

1. A method for predicting a critical caking cycle of a crystal particle, wherein the method is executed by a processor, the method comprises:

establishing a CHS crystal bridge growth model database of a crystal particle with a same type of a crystal particle to be predicted, wherein the CHS crystal bridge growth model database includes: an equivalent particle radius corresponding to different particle size standards of the same type of crystal particles, a moisture absorption capacity of crystal particles with different equivalent particle radii under multiple ambient temperatures and multiple ambient humidity conditions, respectively, and reference critical caking cycles of the crystal particles with different equivalent particle radii under the multiple ambient temperatures and multiple humidity cycle conditions, respectively; wherein the CHS crystal bridge growth model includes at least one of a plurality of combinations of the different ambient temperatures and ambient humidity conditions and a plurality of combinations of the different ambient temperatures and humidity cycle conditions;

matching with the CHS crystal bridge growth model database based on an equivalent particle radius, an actual ambient temperature, and an actual humidity cycle condition of the crystal particle to be predicted, respectively, and calculating a critical caking cycle of the crystal particle to be predicted by selecting a corresponding preset algorithm according to a match result; wherein the preset algorithm includes a first preset algorithm and the second preset algorithm;

in response to matching the CHS crystal bridge growth model database based on the actual ambient temperature and the actual humidity cycle condition of the crystal particle to be predicted, obtaining a target same type of crystal particles with a same environmental temperature and humidity cycle condition as the actual environmental temperature and humidity cycle condition, respectively, and determining the critical caking cycle of the crystal particle to be predicted through the first preset algorithm according to equation (a):

$$\frac{N_1}{N_1'} = \left(\frac{R_{1e}}{R_{1e}'}\right)^4, \quad \text{equation (a)}$$

in the equation (a), $R_{1e}$ represents an equivalent particle radius of the target same type of crystal particles, $R_{1e}'$ represents the equivalent particle radius of the crystal particle to be predicted, $N_1$ represents a reference critical caking cycle of the target same type of crystal particles under the actual environmental temperature and humidity cycle condition of the crystal particle to be predicted, M' represents the critical caking cycle of the crystal particle to be predicted, and $N_1$ and M' are an integer not less than 1, respectively;

in response to matching the CHS crystal bridge growth model database based on the actual ambient temperature and the equivalent particle radius of the crystal particle to be predicted, obtaining a target same type of crystal particles with a same environmental temperature and equivalent particle radius as the actual environmental temperature and equivalent particle radius, respectively, and determining the critical caking cycle of the crystal particle to be predicted through the second preset algorithm according to equation (b):

$$\frac{N_2}{N_2''} = \frac{V_I'}{V_I}, \quad \text{equation (b)}$$

wherein, $$V_I = V_{RH2} - V_{RH1}, \quad \text{equation (c);}$$

$$V_I' = V_{RH3} - V_{RH1}, \quad \text{equation (d);}$$

in the equation (b), $V_{RH2}$ represents a moisture absorption capacity of the target same type of crystal particles under a high humidity condition in a corresponding humidity cycle condition; $V_{RH3}$ represents a moisture absorption capacity of the target same type of crystal particles under a high humidity condition in the actual humidity cycle condition, wherein a low humidity condition in the corresponding humidity cycle condition is the same as a low humidity condition in the high humidity condition in the actual humidity cycle condition; $V_{RH1}$ represents a moisture absorption capacity of the target same type of crystal particles under a low humidity condition in the corresponding humidity cycle condition; $V_I$ represents a difference between the moisture absorption capacity of the target same type of crystal particles under the high humidity condition and the low humidity condition in the corresponding humidity cycle condition; $V_I'$ represents a difference between the moisture absorption capacity of the same type of crystal particles between the high humidity condition and the low humidity condition in the actual humidity cycle condition; $N_2$ represents a reference critical caking cycle of the target same type of crystal particles in the corresponding humidity cycle condition; $N_2''$ represents a reference critical caking cycle of the target same type of crystal particles in the actual humidity cycle condition, and $N_2$ and $N_2''$ are an integer not less than 1, respectively;

wherein the high humidity condition in the multiple humidity cycle conditions in the CHS crystal bridge growth model database is lower than a deliquescence point of the target same type of crystal particles such that the reference critical caking cycle is greater than once when a particle size of the target same type of crystal particles is less than 100 microns, the low humidity condition in the multiple humidity cycle conditions is less than the high humidity condition, and a humidity difference between the low humidity condition and the high humidity condition is greater than 20%;

wherein the reference critical caking cycle of the target same type of crystal particles with different equivalent particle radii under the multiple ambient temperatures and multiple humidity cycle conditions is obtained by:

loading the target same type of crystal particles into a caking mold and placing the caking mold in a box with a set temperature, setting a high humidity and low humidity in a high and low humidity cycle within the box being the same with the humidity cycle condition of the target same type of crystal particles, and setting a period of the high and low humidity cycle to 12-24 hours;

counting a time of the high and low humidity cycle, and performing a de-molding operation for a caking of the target same type of crystal particles in the caking mold;

during the de-molding operation, in response to the caking falling apart, determining that the caking of the target same type of crystal particles is not caked, and continuing to perform above cycle to a next cycle until the caking does not fall apart, and determining a count of cycles completed to prevent the caking from falling apart as a reference critical caking cycle of the target same type of crystal particles under a corresponding ambient temperature and humidity cycle condition.

2. The method for predicting the critical caking cycle of the crystal particle of claim 1, wherein the equivalent particle radius of the target same type of crystal particles and the equivalent particle radius of the crystal particle to be predicted in the CHS crystal bridge growth model database are obtained by following operations:

obtaining at least one particle size interval by performing particle size screening on crystal particles to be measured; determining a crystal quality and a count of crystal particles of the at least one particle size interval, and calculating an equivalent particle radius Re of the crystal particles to be measured according to equations (e) and (f)

$$P_1 R_1^3 + P_2 R_2^3 + \ldots + P_n R_n^3 = (P_1 + P_2 + \ldots + P_n) R_e^3, \quad \text{equation (e);}$$

$$P_1 R_1^3 : P_2 R_2^3 : \ldots : P_n R_n^3 = m_1 : m_2 : \ldots : m_n, \quad \text{equation (f);}$$

wherein $m_1, m_2, \ldots, m_n$ represent a crystal quality of (1-n)th particle size intervals, respectively, $P_1, P_2, \ldots, P_n$ represent a count of crystal particles of the (1-n)th particle size intervals, respectively, $R_1, R_2, \ldots, R_n$ represent a median radius value of the (1-n)th particle size intervals, respectively, n represents a count of particle size intervals, and Re represents the equivalent particle radius of the crystal particles.

3. The method for predicting the critical caking cycle of the crystal particle of claim 1, wherein the determining the count of cycles completed to prevent the caking from falling apart as the reference critical caking cycle of the target same type of crystal particles under the corresponding ambient temperature and humidity cycle condition includes:

in a same condition, determining the reference critical caking cycle repeatedly for three times, calculating an average of the reference critical caking cycles determined by three times, and designating the average as a reference critical caking cycle after averaging treatment.

4. The method for predicting the critical caking cycle of the crystal particle of claim 1, wherein $V_{RH1}$, $V_{RH2}$, and $V_{RH3}$ in the equation (c) and equation (d) are calculated by:

under a same ambient temperature, a same environmental humidity, and different equivalent particle radii, calculating a moisture absorption capacity $V_{RH}'$ of a target same type of crystal particle with an equivalent particle radius $R_e'$ under an environmental humidity condition RH based on following equation (g):

$$\frac{V_{RH}}{V_{RH}'} = \frac{R_e}{R_e'}, \quad \text{equation (g)}$$

wherein $V_{RH}$ represents a moisture absorption capacity of the target same type of crystal particles with the equivalent particle radius Re under the environmental humidity condition RH in the CHS crystal bridge growth model database, and $V_{RH}'$ is one of $V_{RH1}$, $V_{RH2}$, and $V_{RH3}$.

5. The method for predicting the critical caking cycle of the crystal particle of claim 1, wherein a determination of the moisture absorption capacity of the target same type of crystal particles is performed by a dynamic steam adsorption instrument, before the determination, performing an initial drying treatment for the target same type of crystal particles in advance, and a mass of the target same type of crystal particles does not exceed 10 mg.

6. The method for predicting the critical caking cycle of the crystal particle of claim 1, wherein the crystal particle includes a xylitol crystal particle, and a high humidity condition of the humidity cycle condition for the xylitol crystal particle is 65% and a low humidity condition of the humidity cycle condition for the xylitol crystal particle is 30%.

* * * * *